US010702484B2

(12) United States Patent
Krammer et al.

(10) Patent No.: US 10,702,484 B2
(45) Date of Patent: Jul. 7, 2020

(54) USE OF 3-(3-HYDROXY-4-METHOXY-PHENYL)-1-(2,4,6-TRIHYDROXY-PHENYL) PROPAN-1-ONE

(71) Applicant: SYMRISE AG, Holzminden (DE)

(72) Inventors: Gerhard Krammer, Holzminden (DE); Jakob Ley, Holzminden (DE); Fabia Hentschel, Holzminden (DE); Susanne Paetz, Höxter (DE); Thomas Riess, Holzminden (DE); Michael Backes, Holzminden (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 16/071,295

(22) PCT Filed: Apr. 28, 2016

(86) PCT No.: PCT/EP2016/059568
§ 371 (c)(1),
(2) Date: Jul. 19, 2018

(87) PCT Pub. No.: WO2017/186299
PCT Pub. Date: Nov. 2, 2017

(65) Prior Publication Data
US 2019/0343777 A1 Nov. 14, 2019

(51) Int. Cl.
*A61K 31/12* (2006.01)
*A23L 27/00* (2016.01)
*A23L 27/26* (2016.01)
*A23L 27/30* (2016.01)
*A23L 27/60* (2016.01)
*A23L 27/20* (2016.01)
*A23G 3/38* (2006.01)
*A23G 4/06* (2006.01)
*A23L 2/56* (2006.01)
*A23L 2/60* (2006.01)

(52) U.S. Cl.
CPC ............... *A61K 31/12* (2013.01); *A23G 3/38* (2013.01); *A23G 4/06* (2013.01); *A23L 2/56* (2013.01); *A23L 2/60* (2013.01); *A23L 27/204* (2016.08); *A23L 27/26* (2016.08); *A23L 27/33* (2016.08); *A23L 27/63* (2016.08); *A23L 27/84* (2016.08); *A23L 27/86* (2016.08); *A23L 27/88* (2016.08); *A23V 2002/00* (2013.01)

(58) Field of Classification Search
None
See application file for complete search history.

(56) References Cited

U.S. PATENT DOCUMENTS

| 3,743,716 A | 7/1973 | Rizzi et al. |
| 3,867,557 A | 2/1975 | Neely et al. |

FOREIGN PATENT DOCUMENTS

| CN | 101237850 A | 8/2008 |
| FR | 2865900 A1 | 8/2005 |
| JP | S5512232 B1 | 3/1980 |
| JP | 2002275468 A | 9/2002 |
| JP | 2003321351 A | 11/2003 |
| JP | 2004018376 A | 1/2004 |
| JP | 2004043354 A | 2/2004 |
| JP | 2006056831 A | 3/2006 |
| JP | 2009502984 A | 1/2009 |
| WO | 2007014476 A | 2/2007 |

OTHER PUBLICATIONS

International Search Report and Written Opinion dated Jan. 24, 2017 for corresponding PCT Application No. PCT/EP2016/059568.
Japanese Office Action dated Mar. 2, 2020 for corresponding Japanese Application No. 2018-544933.
DuBois et al., "N,N-Dimethyl-1-(p-chlorophenyl)-4-(cycloalkylalkyl)-4-hydroqcyclohexylamines," Journal of Medical Chemistry, vol. 24, No. 4, 1981; pp. 408-428.
DuBois et al., "Nonnutritives sweeteners: taste-structure relationships for some new simple dihydrochalcones," Science; vol. 195, 1977; pp. 397-399.

*Primary Examiner* — Samantha L Shterengarts
(74) *Attorney, Agent, or Firm* — Polsinelli PC

(57) ABSTRACT

The present invention concerns the use of 3-(3-Hydroxy-4-methoxy-phenyl)-1-(2,4,6-trihydroxyphenyl)propan-1-one for masking, reducing or suppressing an unpleasant taste impression, preferably bitter, sour and/or astringent taste impression of unpleasant-tasting substances or mixture of substances, preferably bitter-, sour-, and/or astringent-tasting substances or mixtures of substances, and in particular the bitter taste impression of bitter-tasting substances, and/or modulating the taste impressions selected from the group consisting of cooling, umami, fruity and spicy notes of cooling-, umami-, fruity- or spicy-tasting substances or mixture of substances, and simultaneously intensifying the sweet-taste impression of sweet-tasting substances or mixtures of substances or both sweet- and bitter-tasting tasting substances or mixture of substances.

12 Claims, No Drawings

USE OF 3-(3-HYDROXY-4-METHOXY-PHENYL)-1-(2,4,6-TRIHYDROXY-PHENYL) PROPAN-1-ONE

CROSS-REFERENCE TO RELATED APPLICATIONS

This application is a national stage application (under 35 U.S.C. § 371) of PCT/EP2016/059568, filed Apr. 28, 2016, which is incorporated herein by reference in its entirety.

The present invention concerns the use of 3-(3-Hydroxy-4-methoxy-phenyl)-1-(2,4,6-trihydroxyphenyl)propan-1-one (compound of Formula (I)), in the following referred to as hesperetin dihydrochalcone (I), wherein (I) is understood to be a reference to Formula (I),

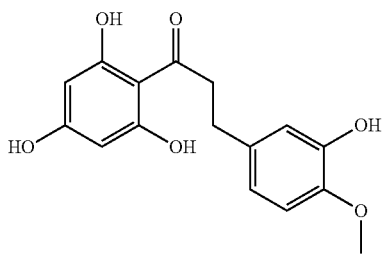

(I)

or a salt of hesperetin dihydrochalcone (I) or a mixture comprising or consisting of a plurality of salts of the hesperetin dihydrochalcone (I) or a mixture comprising or consisting of hesperetin dihydrochalcone (I) and a salt or a plurality of salts of the hesperetin dihydrochalcone (I) for
(i) masking, reducing or suppressing an unpleasant taste impression, preferably bitter, sour and/or astringent taste impression of unpleasant-tasting substances or mixture of substances, preferably bitter-, sour-, and/or astringent-tasting substances or mixtures of substances, and in particular the bitter taste impression of bitter-tasting substances, and/or
(ii) modulating the taste impressions selected from the group consisting of cooling, sweet, umami, fruity and spicy notes of cooling-, sweet-, umami-, fruity- or spicy-tasting substances or mixture of substances.

The present invention also concerns aroma compositions comprising hesperetin dihydrochalcone (I) or a salt of the hesperetin dihydrochalcone (I) or a mixture comprising or consisting of a plurality of salts of the hesperetin dihydrochalcone (I) or a mixture comprising or consisting of hesperetin dihydrochalcone (I) and a salt or a plurality of salts of the hesperetin dihydrochalcone (I).

The present invention also concerns preparations, in particular preparations serving for nutrition, as food supplements, for oral care or for pleasure, as cosmetics or pharmaceuticals for oral administration as well as intermediate goods comprising such an aroma composition.

In addition, the present invention concerns a method for manufacturing such aroma compositions, such preparations or such intermediate goods.

Furthermore, the present invention concerns a method for masking, reducing or suppressing an unpleasant taste impression, preferably bitter, sour and/or astringent taste impression of unpleasant-tasting substances or mixture of substances, preferably bitter-, sour-, and/or astringent-tasting substances or mixtures of substances, and in particular the bitter taste impression of bitter-tasting substances.

In addition, the present invention also concerns a method for modulating the taste impressions selected from the group consisting of cooling, sweet, umami, fruity and spicy notes of cooling-, sweet-, umami-, fruity- or spicy-tasting substances or mixture of substances.

Further aspects of the present invention and preferred embodiments of it will emerge from the following description and the attached claims.

STATE OF THE ART

Foodstuffs or semi-luxury products, with a high sugar content (especially sucrose (=saccharose), lactose, glucose or fructose or mixtures of these), are generally particularly preferred by consumers because of their sweetness. On the other hand, it is well known that a high content of carbohydrates which are easy to metabolize results in a sharp increase in the blood sugar level, and the formation of fatty deposits and ultimately can lead to health problems such as obesity, adiposity, insulin-resistance, adult-onset diabetes and the associated conditions of these. In particular this is compounded by the fact that many of the stated carbohydrates can also have an adverse effect on dental health, since they are broken down in the oral cavity by certain kinds of bacteria into lactic acid, for example, which can attack the dental enamel of young and adult teeth (tooth decay).

It has therefore long been an objective to reduce the sugar content of foodstuffs and/or semi-luxury foods to the absolute minimum or below. One such measure is the use of sweeteners. These are substances which in themselves have no or only a very low calorific value and which at the same time bring about a strong sweet taste impression; these substances are as a rule non-cariogenic (an overview can be found, by way of example, in the *Journal of the American Dietetic Association* 2004, 104 (2), 255-275).

So-called bulk sweeteners such as sorbitol, mannitol or other sugar alcohols are indeed to some extent exceptional sweeteners and can also partly replace the other characteristics of sugar for food technology purposes, but if these are ingested too often they can cause osmotic related digestive problems in some people.

Non-nutritious, highly intensive sweeteners are in fact, due to their low usage concentration, well suited to providing sweetness in foodstuffs, but often demonstrate taste problems due to a time-intensity profile that differs from that of sugar (e.g. sucralose, steviosides, cyclamate), a bitter and/or astringent aftertaste (e.g. acesulfame K, saccharin, stevioside, rebaudioside) and/or pronounced additional flavour impressions (e.g. glycyrrhizic acid ammonium salt). Some of these sweeteners are not particularly stable under heat (e.g. thaumatin, brazzein, monellin), are not stable in all applications (e.g. aspartame) and in some cases have a long-lasting sweetening effect (strong sweet aftertaste, e.g. saccharin, sucralose). An alternative—without using non-nutrient sweeteners—consists of lowering the sugar content of foodstuffs and/or semi-luxury foods and using sensorically weak or imperceptible substances, which intensify the sweetness indirectly or directly.

In WO 2007/014879 A1 the use of hesperetin and in WO 2007/107596 A1 phloretin as an intensifier of the sweet flavour of sugar-reduced preparations for food or pleasure is recommended. Occasionally, however, when using hesperetin and phloretin the comparative weakness of the intensification of sweetness in foodstuffs and semi-luxury foods e.g. in yogurt products, containing high proportions of proteins, in particular denatured proteins or polysaccharides, can be a disadvantage. Hesperetin also has the disadvantage in very acidic and carbonized applications such as lemonades and cola drinks, that it is not sufficiently effective.

Further, foodstuffs or semi-luxuries often contain various unpleasant-tasting substances, e.g. bitter substances, strongly sour substances and astringent substances, which on the one hand in moderation are desirable and characteristic (e.g. caffeine in tea or coffee, tannins in red wine or green tea, quinine in so-called bitter-lemon beverages, saponins or isoflavonoids or glycosides thereof in soya milk, hop extracts in beer, fruit acids or edible acids in sweet fruit juices), but on the other hand can also greatly reduce the value (e.g. flavonoid glycosides and limonoids in citrus juices, bitter and/or astringent aftertaste of many artificial sweeteners such as aspartame or saccharin, hydrophobic amino acids and/or peptides in cheese, fruit acids or edible acids without sufficient toning down by sweet flavouring materials, e.g. in milk products containing lactic acid). Often the unpleasant taste is further intensified by unpleasant odors, for example in soya milk, which often has a bitter and astringent taste, a note generally designated as "beany" is also described as unpleasant.

Bitter taste is regularly caused by particular substances, which bind to special bitter receptors on taste cells (which are to be found in the so-called taste buds on the tongue) and, via neurochemical cascades, send a signal to the brain, which causes a defense reaction and a negative taste impression (cf. Wolfgang Meyerhof, *Reviews of Physiology, Biochemistry and Pharmacology* 2005, 154, 37-72).

Astringent taste is as a rule caused by precipitation of proline-rich proteins in the saliva by astringents, e.g. metal salts or tannins. The normally homogeneous saliva that serves as a "lubricant" then contains denatured proteins, which reduce the lubricity and so leave a rough or dry sensation in the mouth, which is also experienced as astringent (Isabelle Lesschaeve, Ann C. Noble, *American Journal of Clinical Nutrition* 2005, 81, 330S335S).

Sour taste is caused by protic acids. The so-called titratable proton concentration is then more decisive than the pH for the sour impression: for example, a hydrochloric acid solution with the same pH as a malic acid solution tastes far less sour in comparison. Classically, the aversive sour taste is toned down considerably by combining with sweet flavouring materials, principally sugar, or even by substances that taste salty, mainly sodium chloride, whereas the sour taste is perceived as much more unpleasant with bitter or astringent tasting substances. However, sweet-tasting substances (for example sweeteners) are regularly used at comparatively high concentrations, thus as a rule in an amount which, with respect to their sweet taste impression, would correspond to an at least 2 wt. % aqueous sucrose solution, to achieve a marked toning-down of the sour impression.

Some fruit acids, in particular citric acid, succinic acid, malic acid and tartaric acid, also produce a sensory impression described as astringent, along with the sour taste.

In some foodstuffs, in particular foodstuffs derived from sweet-sour fruits or vegetables (e.g. fruit juices, fruit preparations and foodstuffs produced from them) and products produced by fermentation by acid-producing microorganisms (e.g. yogurt, ghee, kefir, soyayogurt, sauerkraut, sourdough bread, sausages, sour milk, cheese, mixed pickles, refreshing drinks containing lactobionic acid or glucuronic acid), the acid content is necessary to produce microbial stability. Up to a certain degree this is accepted as regards taste, but in many cases there is a desire to achieve a reduced sour sensory impression without affecting the pH, which is required for the keeping qualities. We must also consider foodstuffs for which, in order to achieve a sufficient microbial or also antioxidative stability, the pH is adjusted with fruit acids or edible acids (e.g. apple juice with ascorbic acid, refreshing drinks with citric or phosphoric acid, dressings and ketchup with acetic acid), but the sour taste is regularly perceived as too strong and should therefore be reduced in sensory terms.

To summarize, it can be stated that there are various foods or foodstuffs that produce a sour sensory impression that is too high, i.e. higher than desired, which is caused by the natural concentration of fruit acids, acids formed by fermentation or acids added for reasons of stability, and where the pH of the foods or foodstuffs cannot or should not be altered for technological reasons (microbial stability, antioxidative stability etc., as explained above).

It has been described in the prior art that certain proteins such as miraculin can, in the presence of acids, transform the sour impression more or less into a sweet taste impression (http://de.wikipedia.org/wiki/Miraculin). However, because of conversion to the sweet taste, which is undesirable in non-sweet applications, this solution is only of limited use and moreover lasts too long, at 2-4 h, so that this effect is only of very restricted benefit.

Non-nutrient, highly intensive sweeteners often exhibit taste problems. The steviol glycosides (for example stevioside, rebaudioside A-Z [A, B, C, D, E, F, G, H, I, O, M, N, V, W, X, Z, KA, etc.], steviolbioside, dulcoside A, dulcoside B, rubusoside, suavioside A, B and G-J) naturally occurring in *Stevia* ssp. or *Rubus* ssp., while being very good sweeteners, at the concentrations necessary for an adequate sweetening effect (for example 400-600 ppm for rebaudioside A [purity>90%] in soft drinks, in order to achieve a sweetness corresponding to a concentration of sucrose of 10% by weight) already exhibit a pronounced licorice-like and unpleasant bitter and astringent off-taste and/or aftertaste.

In particular in sweet, calorie-free or low-calorie drinks, which have been manufactured with the help of such sweeteners, this unpleasant off-taste and/or aftertaste frequently lowers the sensory acceptance and should therefore be masked.

In the literature a number of possibilities have been offered for this. Thus in US 2004/0142084 alkaline metal hydrogen sulphates are described as masking agents. These increase the acid content in applications sharply, however. In U.S. Pat. No. 3,924,017 caffeic acid derivatives have been proposed for masking. The disadvantage is that caffeic acid itself has a slightly bitter taste and easily suppresses the sweetness, so that more sweeteners would have to be used.

In WO 2006/087991 the unpleasant taste is suppressed by alkamides such as spilanthol; often, however, the tingling effect of this substance group is not desired here so that these do not have wide application.

An improvement in the taste features, in particular concerning the problem of aftertaste of non-nutrient, high intensity sweeteners can be achieved by using tannic acid, e.g. as described in WO 98/20753, or phenolic acids, e.g. as described in U.S. Pat. No. 3,924,017. However, because of their catechol units such substances are not particularly stable in applications and as typical astringents intensify a bitter and/or astringent off-taste and/or aftertaste.

Not only the above-mentioned steviol glycosides, but also other substances, with a bitter taste or aftertaste, can in foodstuffs or semi-luxury foods sharply reduce the quality of these (e.g. flavonoid glycosides and limonoids in citrus juices, artificial sweeteners such as aspartame or saccharin, hydrophobic amino acid and/or peptides in cheese), even though substances with such taste directions may be desirable in moderation and characteristic of such foodstuffs or semi-luxury foods (e.g. caffeine in tea and coffee, quinine in so-called bitter lemon drinks, hop extracts in beer).

In particular to lower the natural content of bitter substances a subsequent treatment is therefore often necessary, for example extractively such as with the decaffeination of tea or coffee, or enzymatically, such as for example with the treatment of orange juice with a glycosidase in order to destroy the bitter naringin or use of special peptidases in the ripening of cheese. This treatment places a strain on the product, generates waste materials and also causes, for example, solvent residues and other residues (enzymes) in the products.

The relationships between structure and sweetening power were investigated as far back as 1979 (*J. Chem. Senses* 1979, 4(1), 35-47). It was found that the 3-hydroxy-4-methoxy-phenyl group represents an important condition for a powerful sweetener, and reversing the substituents is associated with a loss of sweetening power. The intensively sweet tasting dihydrochalcone (2) and the surprisingly tasteless dihydrochalcone (3) are presented in this publication. The hesperetin dihydrochalcone (I) itself, as well as potential masking or sweetness intensifying features of these compounds are not described.

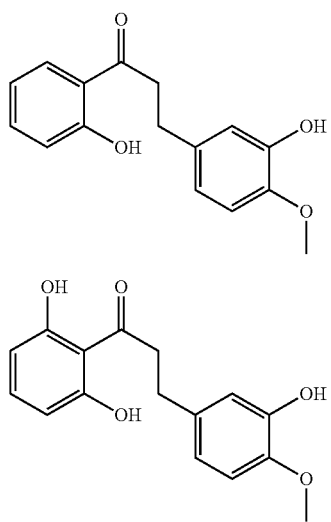

The compound (I) itself is known from the literature and is described, inter alia, in *J. Agric. Food Chem.* 1977, 25(4), 763-772, as a sweet-tasting substance. This publication is however focused on sulfonate derivatives of hesperetin dihydrochalcone (I) and their sensory evaluation. No further sensory effects of compound (I) are described.

Compound (I) is likewise mentioned in the publication *J. Med. Chem.* 1981, 24(4), 408-428, which similarly deals with sweeteners based on a dihydrochalcone structure. The importance of the 3-hydroxy-4-methoxy-phenyl group for a clear sweetness impression is also emphasized here, and furthermore the 2,6-dihydroxy-substitution pattern of the remaining aromatic compounds is assumed to be particularly important for a strong sweetness impression. No further sensory effects of compound (I) are described.

Compound (I) and other ring-substituted hesperetin dihydrochalcones are described in *J. Agric. Food. Chem* 1991, 39(1), 44-51 and their sweet intensity compared to a 6% aqueous sucrose solution wherein a similar or weaker sweet intensity for compound (I) is described. No further sensory effects of compound (I) are described.

*J. Chem. Soc., Perkin Trans.* 2 1998, 6, 1449-1454 describes a three-dimensional binding-site model for the structurally uncharacterised sweet-taste receptor, using pseudoreceptor modelling. The receptor model was derived based on 17 sweet compounds of the isovanillyl class (4-methoxy-3-hydroxybenzyl), inter alia compound (I), as the training set and consists of nine key amino-acid residues embedded in a hydrophobic receptor cavity. *Quant. Struct.-Act. Relat.* 2001, 20(1), 3-16 describes the results obtained by applying statistical models to develop QSARs for Isovanillyl derivatives. Compound (I) was here described, however compound (I) was not considered in the sensory evaluation.

It is important to mention that the literature referred to compound (I) the focus is drawn to the development of potential sweeteners. There is no hint to an effect of compound (I) in combination with sweet-modulating substances or other sweeteners as well as to an effect of compound (I) in combination with other fragrances or flavours (e.g. bitter-tasting substances).

In this context is merely known that the sweetness intensifying feature of dihydrochalcone-compounds differs from one to another.

In patent application WO2007/107596 A1,4-hydroxydihydrochalcones of Formula (7) and their salts are described for the intensification of sweet sensorial impressions.

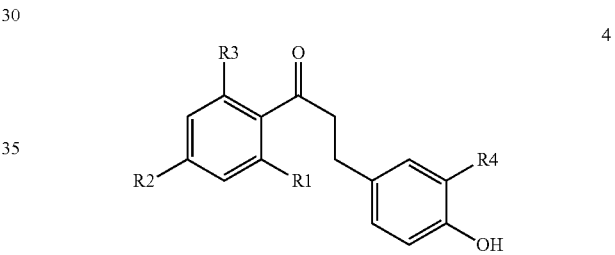

wherein R1, R2, R3 and R4 independently of one another denote H, OH or O-alkyl (with preferably 1-4 C-atoms, i.e. preferably $C_1$ to $C_4$ alkoxy), respectively, on condition that at least one of the residues R1, R2 or R3 signifies OH. However, for the sweetness-intensifying effects found here a 4-hydroxy-substitution was necessary.

It is particularly important to suppress an unpleasant taste impression, in particular a bitter taste impression, in many pharmaceutical active substances, since in this way the readiness of patients, in particular patients sensitive to a bitter taste such as children, to take the preparation orally, can be considerably increased. Many pharmaceutically active substances such as fluoroquinolone antibiotics, beta-lactam antibiotics, ambroxol, propylthiouracil [PROP], aspirin (acetyl salicylic acid), salicin, paracetamol (acetaminophene), ibuprofen, naproxen, ambroxol, guafenesin, omeprazole, pantoprazole, dextromorphane or quinine, to name but a few and for clarification purposes, have a pronounced bitter, astringent and/or metallic taste or aftertaste.

There is therefore a need to provide substances which in low concentrations effectively intensify sweet taste impressions of sweet substances, preferably the sweet taste impression of sugar-reduced foodstuffs and semi-luxury foods, in particular of sugar-reduced foodstuffs and semi-luxury foods with a low pH value, without adversely affecting the flavour profile.

Further, there is a need to provide substances that are able to mask, reduce or suppress the bitter, sour and/or astringent taste impression of compounds, also in preparations, in particular in foodstuffs and semi-luxuries and medicinal products, preferably without substantially affecting the otherwise desirable taste impression of these preparations.

The primary object of the present invention was therefore to provide substances that are able in low concentrations to mask, reduce or suppress an unpleasant taste impression, preferably bitter, and/or sour and/or astringent taste impression of unpleasant-tasting substances or mixture of substances, preferably bitter-, and/or sour-, and/or astringent-tasting substances or mixtures of substances, and in particular the bitter impression of bitter-tasting substances.

A further object of the present invention was to provide substances which in low concentrations are able to modulate the taste impressions selected from the group consisting of cooling, sweet, umami, fruity and spicy notes of cooling-, sweet-, umami-, fruity- or spicy-tasting sub-stances or mixtures of substances.

A further object of the present invention was to provide substances that are able in low concentrations to mask, reduce or suppress an unpleasant taste impression, preferably bitter, and/or sour and/or astringent taste impression of unpleasant-tasting substances or mixture of substances, preferably bitter-, and/or sour-, and/or astringent-tasting substances or mixtures of substances, and in particular the bitter impression of bitter-tasting substances and to modulate the taste impressions selected from the group consisting of cooling, sweet, umami, fruity and spicy notes of cooling-, sweet-, umami-, fruity- or spicy-tasting sub-stances or mixtures of substances.

A further object of the present invention was to provide substances that are able in low concentrations to mask, reduce or suppress an unpleasant taste impression, preferably bitter, and/or sour and/or astringent taste impression of unpleasant-tasting substances or mixture of substances, preferably bitter-, and/or sour-, and/or astringent-tasting substances or mixtures of substances, and in particular the bitter impression of bitter-tasting substances and simultaneously to intensify—preferably synergistically— the sweet-taste impression of sweet-tasting substances or mixtures of substances or both sweet- and bitter-tasting tasting substances or mixture of substances.

A further object of the present invention was to provide substances which in low concentrations are able to modulate the taste impressions selected from the group consisting of cooling, sweet, umami, fruity and spicy notes of cooling-, sweet-, umami-, fruity- or spicy-tasting sub-stances or mixtures of substances and simultaneously to intensify—preferably synergistically—the sweet-taste impression of sweet-tasting substances or mixtures of substances or both sweet- and bitter-tasting tasting substances or mixture of substances.

A further object of the present invention was to provide substances that are able in low concentrations to mask, reduce or suppress an unpleasant taste impression, preferably bitter, and/or sour and/or astringent taste impression of unpleasant-tasting substances or mixture of substances, preferably bitter-, and/or sour-, and/or astringent-tasting sub-stances or mixtures of substances, and in particular the bitter impression of bitter-tasting substances and simultaneously to intensify—preferably synergistically—the sweet-taste impression of sweet-tasting substances or mixtures of substances or both sweet- and bitter-tasting tasting substances or mixture of substances and further are able to modulate the taste impressions selected from the group consisting of cooling, sweet, umami, fruity and spicy notes of cooling-, sweet-, umami-, fruity- or spicy-tasting substances or mixtures of substances.

DESCRIPTION OF THE INVENTION

An aspect of the present invention is the use of 3-(3-Hydroxy-4-methoxy-phenyl)-1-(2,4,6-trihydroxyphenyl) propan-1-one (compound of Formula (I)), in the following referred to as hesperetin dihydrochalcone (I)

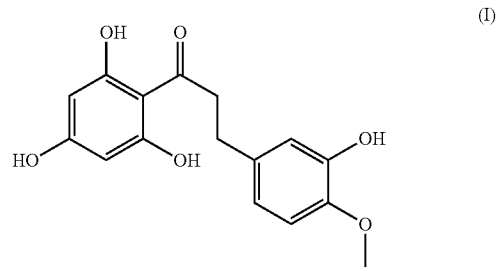 [SMILES: COc1ccc(CCC(=O)c2c(O)cc(O)cc2O)cc1O]

or
a salt of hesperetin dihydrochalcone (I) or a mixture comprising or consisting of a plurality of salts of the hesperetin dihydrochalcone (I)
or
a mixture comprising or consisting of hesperetin dihydrochalcone (I) and a salt or a plurality of salts of the hesperetin dihydrochalcone (I) for
(i) masking, reducing or suppressing an unpleasant taste impression, preferably bitter, and/or sour and/or astringent taste impression of unpleasant-tasting substances or mixture of substances, preferably bitter-, and/or sour-, and/or astringent-tasting substances or mixtures of substances, and in particular the bitter taste impression of bitter-tasting substances.

In our own investigations in the area of flavanoids and dihydrochalcones it was surprisingly found that hesperetin dihydrochalcone (I) has a masking, reducing or suppressing effect of an unpleasant taste impression selected from the group consisting of bitter, and/or sour and/or astringent taste impression, in particular bitter taste impression. Thus, it was surprisingly found that hesperetin dihydrochalcone (I) is able to mask, reduce or suppress the bitterness of prominent bitter components (cf. example 2).

A further aspect of the present invention is the use of hesperetin dihydrochalcone (I) or
a salt of hesperetin dihydrochalcone (I) or a mixture comprising or consisting of a plurality of salts of the hesperetin dihydrochalcone (I), or
a mixture comprising or consisting of hesperetin dihydrochalcone (I) and a salt or a plurality of salts of the hesperetin dihydrochalcone (I) for
(ii) modulating the taste impressions selected from the group consisting of cooling, sweet, umami, fruity and spicy notes of cooling-, sweet-, umami-, fruity- or spicy-tasting substances or mixture of substances.

According to the present invention the expression "modulating the taste impressions selected from the group consisting of cooling, sweet, umami, fruity and spicy notes of cooling-, sweet-, umami-, fruity- or spicy-tasting substances or mixture of substances" means the improvement of the taste profile, preferably regarding a faster and better perception of cooling, umami, fruity and spicy notes. Accordingly it is possible to modulate the fruity and spicy flavours and notes, so that a more authentic profile can be achieved.

A preferred use according to the present invention is the use of hesperetin dihydrochalcone (I) or
- a salt of hesperetin dihydrochalcone (I) or a mixture comprising or consisting of a plurality of salts of the hesperetin dihydrochalcone (I), or
- a mixture comprising or consisting of hesperetin dihydrochalcone (I) and a salt or a plurality of salts of the hesperetin dihydrochalcone (I) for
(i) masking, reducing or suppressing an unpleasant taste impression, preferably bitter, and/or sour and/or astringent taste impression of unpleasant-tasting substances or mixture of substances, preferably bitter-, and/or sour-, and/or astringent-tasting substances or mixtures of substances, and in particular the bitter taste impression of bitter-tasting substances, and
(ii) modulating the taste impressions selected from the group consisting of cooling, sweet, umami, fruity and spicy notes of cooling-, sweet-, umami-, fruity- or spicy-tasting substances or mixture of substances.

In our own investigations in the area of flavanoids and dihydrochalcones it was surprisingly found that hesperetin dihydrochalcone (I) has a masking, reducing or suppressing effect of an unpleasant taste impression selected from the group consisting of bitter, and/or sour and/or astringent taste impression, in particular bitter taste impression, and further a positive effect in the taste profile of different compositions, in particular aroma compositions. None of prior art documents suggest these effects, especially taken in consideration, that none of these documents teach a modulating effect of taste impressions, in particular bitter, sour, astringent, cooling, umami, fruity and spicy notes.

A preferred use according to the present invention is the use of hesperetin dihydrochalcone (I) or
- a salt of hesperetin dihydrochalcone (I) or a mixture comprising or consisting of a plurality of salts of the hesperetin dihydrochalcone (I), or
- a mixture comprising or consisting of hesperetin dihydrochalcone (I) and a salt or a plurality of salts of the hesperetin dihydrochalcone (I) for
(i) masking, reducing or suppressing an unpleasant taste impression, preferably bitter, and/or sour and/or astringent taste impression of unpleasant-tasting substances or mixture of substances, preferably bitter-, and/or sour-, and/or astringent-tasting substances or mixtures of substances, and in particular the bitter taste impression of bitter-tasting substances, and simultaneously
(iii) intensifying—preferably synergistically—the sweet-taste impression of sweet-tasting substances or mixtures of substances or both sweet- and bitter-tasting tasting substances or mixture of substances.

A further preferred use according to the present invention is the use of hesperetin dihydrochalcone (I) or
- a salt of hesperetin dihydrochalcone (I) or a mixture comprising or consisting of a plurality of salts of the hesperetin dihydrochalcone (I), or
- a mixture comprising or consisting of hesperetin dihydrochalcone (I) and a salt or a plurality of salts of the hesperetin dihydrochalcone (I) for
(ii) modulating the taste impressions selected from the group consisting of cooling, sweet, umami, fruity and spicy notes of cooling-, sweet-, umami-, fruity- or spicy-tasting substances or mixture of substances, and simultaneously
(iii) intensifying—preferably synergistically—the sweet-taste impression of sweet-tasting substances or mixtures of substances or both sweet- and bitter-tasting tasting substances or mixture of substances.

A particularly preferred use according to the present invention is the use of hesperetin dihydrochalcone (I) or
- a salt of hesperetin dihydrochalcone (I) or a mixture comprising or consisting of a plurality of salts of the hesperetin dihydrochalcone (I), or
- a mixture comprising or consisting of hesperetin dihydrochalcone (I) and a salt or a plurality of salts of the hesperetin dihydrochalcone (I) for
(i) masking, reducing or suppressing an unpleasant taste impression, preferably bitter, and/or sour and/or astringent taste impression of unpleasant-tasting substances or mixture of substances, preferably bitter-, and/or sour-, and/or astringent-tasting substances or mixtures of substances, and in particular the bitter taste impression of bitter-tasting substances, and
(ii) for modulating the taste impressions selected from the group consisting of cooling, sweet, umami, fruity and spicy notes of cooling-, sweet-, umami-, fruity- or spicy-tasting substances or mixture of substances, and simultaneously
(iii) for intensifying—preferably synergistically—the sweet-taste impression of sweet-tasting substances or mixtures of substances or both sweet- and bitter-tasting tasting substances or mixture of substances.

Hesperetin dihydrochalcone (I) is advantageously particularly well-suited for masking or reducing or suppressing an unpleasant taste impression, in particular a bitter taste impression of a bitter-tasting substance (see Application example 2).

In addition hesperetin dihydrochalcone (I) is advantageously particularly well-suited to intensification—preferably synergistic intensification—of the sweet taste impression of a sweet-tasting substance and is easily accessible synthetically. A particularly advantageous, sweetness-intensifying effect of compound (I) results, if the sweet-tasting substance, the sweet taste impression of which is to be intensified—preferably synergistically—according to the invention, is a sugar, in particular sucrose, glucose or fructose or a combination of two or all of these sugars. This particularly advantageous synergistic sweetness intensifying effect of hesperetin dihydrochalcone (I) is demonstrated further on by way of example using the intensification of the sweet taste impression of sucrose (see Application example 3).

A particularly preferred use of hesperetin dihydrochalcone (I) according to the present invention involves the intensification—preferably synergistically—of the sweet taste impression of a both sweet-tasting and also unpleasant-, in particular bitter-, sour-, and/or astringent-tasting substance or mixture of substances and the simultaneous reduction or masking of the unpleasant, in particular bitter, sour-, and/or astringent taste impression of the both sweet- and also unpleasant-, in particular bitter-, sour-, and/or astringent tasting substance or mixture of substances.

Also preferred is an use of hesperetin dihydrochalcone (I) or a salt of the hesperetin dihydrochalcone (I) or a mixture comprising or consisting of a plurality of salts of hesperetin dihydrochalcone (I) or a mixture comprising or consisting of hesperetin dihydrochalcone (I) and a salt or a plurality of salts of the hesperetin dihydrochalcone (I), wherein the sweet taste impression of a sweet-tasting substance or mixture of substances or a both sweet- and unpleasant-, preferably bitter-, and/or sour-, and/or astringent-tasting substance or mixture of substances and in particular the bitter taste impression of bitter-tasting substances is intensified, preferably synergistically intensified.

Preferably hesperetin dihydrochalcone (I) (I) or a salt of hesperetin dihydrochalcone (I) or a mixture comprising or consisting of a plurality of salts of hesperetin dihydrochalcone (I) or a mixture comprising or consisting of hesperetin dihydrochalcone (I) and a salt or a plurality of salts of the hesperetin dihydrochalcone (I) is or are used in the manner described above in an aroma composition or in a preparation selected from the group consisting of preparations serving for nutrition, as food supplements, for oral care or pleasure, as cosmetic preparations, in particular for application in the region of the head, pharmaceutical preparations intended to be taken orally, flavouring mixtures and intermediate goods for use in one of the abovementioned aroma compositions, preparations, or semi-finished products for manufacturing one of the preparations mentioned above.

The synthesis of compound (I) is possible for example via an acidic hydrolysis starting from neohesperidin dihydrochalcone (see example 1) by cleavage of the sugar rests rhamnose and glucose. *J. Agric. Food Chem.* 2005, 1782-1790 describes also this degradation of neohesperidin dihydrochalcone by human intestinal bacteria. DE 2148332 A1 describes also the synthesis of compound (I) via conversion of hesperidin in a soluble salt by treating hesperidin with a 10% aqueous solution KOH, subsequent reduction by hydrogen (Pd/C catalyst) and cleavage of the sugar-residues under acidic conditions. Further alternatives for synthesis of compound (I) starting from benzyl-protected precursors involving a reduction by hydrogen with the addition of a catalyst (e.g. Pd/C) are also conceivable (*J. Agric. Food. Chem* 1991, 39(1), 44-51). However, the use of various protective groups, other bases, different reducing agents and the performing of an acid catalyzed aldol reaction are also possible and obvious to a person skilled in the art.

With the salts of the hesperetin dihydrochalcone (I) to be used according to the present invention one, two or three hydroxy groups can be deprotonated, with a corresponding number of counter cations being present, wherein these are preferably selected from the group consisting of: singly positively charged cations of the first main and subsidiary group, ammonium ions, trialkylammonium ions, doubly positively charged cations of the second main and subsidiary group and triply positively charged cations of the third main and subsidiary group, as well as mixtures of these. Preferably it is a case with these counter cations of cations selected from the group consisting of $Na^+$, $K^+$, $NH_4^+$, $Ca^{2+}$, $Mg^{2+}$, $Al^{3+}$ and $Zn^{2+}$, particularly preferred selected from the group consisting of $Na^+$ and $K^+$.

Consequently, particular preference according to the present invention is for the use of a salt or a mixture of
two or more different salts of the hesperetin dihydrochalcone (I) or
hesperetin dihydrochalcone (I) and one or a plurality of different salts of hesperetin dihydrochalcone (I), as described above, wherein the counter cation(s) of the, one, a plurality of or all the salts of the hesperetin dihydrochalcone (I) is or are selected from the group consisting of $Na^+$, $K^+$, $NH_4^+$, $Ca^{2+}$, $Mg^{2+}$, $Al^{3+}$ and $Zn^{2+}$, particularly preferred selected from the group consisting of $Na^+$ and $K^+$.

For the salts upon which the hesperetin dihydrochalcone (I) is based, that stated above applies accordingly.

In our own investigations in connection with the present invention, it was surprisingly found that hesperetin dihydrochalcone (I) (advantageously even at just very low concentrations) can (in the ideal case completely) mask or (at least) reduce the unpleasant taste impression, in particular the bitter taste impression of a number of unpleasant or bitter-tasting substances, in particular of methylxanthines, such as, for example, caffeine, alkaloids, such as, for example, quinine, flavonoids, such as, for example, catechins, naringin, neohesperidin, phenol glycosides, such as, for example, salicin, arbutin, amygdalin or phenols, such as, for example, hydroxytyrosol or oleuropein, inorganic salts, such as potassium chloride or magnesium sulfate, pharmaceutical active substances, such as, for example, fluoroquinolone antibiotics, beta-lactam antibiotics, ambroxol, propylthiouracil [PROP], aspirin (acetyl salicylic acid), salicin, paracetamol (acetaminophene), ibuprofen, naproxen, ambroxol, guafenesin, omeprazole, pantoprazole, dextromorphane, or quinine, or steviolglycosides, such as, for example, stevioside or rebaudiosides. The masking or reduction of the bitter taste impressions of the compounds mentioned in this paragraph is also preferred according to the invention.

Here it is particularly advantageous for the hesperetin dihydrochalcone (I) to be used according to the invention not to have any complexing features. Hesperetin dihydrochalcone (I) is consequently advantageously particularly well suited to both intensifying a pleasant taste impression, in particular the sweet taste impression of a sweet-tasting substance, preferably in a synergistic manner, and also masking or reducing an unpleasant taste impression, in particular the bitter taste impression of a bitter-tasting substance, wherein preferably both effects occur simultaneously.

A further aspect related to the present invention, therefore concerns the use
(a) of hesperetin dihydrochalcone (I), or
    a salt of the hesperetin dihydrochalcone (I) or a mixture comprising or consisting of a plurality of salts of the hesperetin dihydrochalcone (I), or
    a mixture comprising or consisting of hesperetin dihydrochalcone (I) and a salt or a plurality of salts of the hesperetin dihydrochalcone (I), as described in each case above,
in a mixture comprising at least one or a plurality of the substances selected from the group consisting of substance(s) (c) and (d) or mixtures thereof, wherein
    substance(s) (c) means one or more unpleasant-tasting substances, preferably bitter-, sour-, and/or astringent-tasting substances, in particular bitter-tasting substances
    substance(s) (d) means one or more both sweet-tasting substances and unpleasant-tasting substances, in particular bitter-tasting substances; and/or
    one or more sweet-tasting substances (b)
(a) for the intensification—preferably synergistic intensification—of the sweet taste of the substance(s) (b) or (d), and/or
(b) for masking or reducing the unpleasant taste impression of the unpleasant-tasting substance(s) (c) or (d).

A further aspect related to the present invention, therefore concerns the use
(a) of hesperetin dihydrochalcone (I), or
    a salt of the hesperetin dihydrochalcone (I) or a mixture comprising or consisting of a plurality of salts of the hesperetin dihydrochalcone (I), or
    a mixture comprising or consisting of hesperetin dihydrochalcone (I) and a salt or a plurality of salts of the hesperetin dihydrochalcone (I), as described in each case above, in a mixture comprising at least one or a plurality of the substances selected from the group consisting of substance(s) (c) and (d) or mixtures thereof, wherein substance(s) (c) means one or more unpleasant-tasting substances, preferably bitter-, sour-, and/or astringent-tasting substances, in particular bitter-tasting substances substance(s) (d) means one or more both sweet-tasting substances and unpleasant-tasting substances, in particular bitter-tasting substances; and/or one or more sweet-tasting substances (b)

(a) for the intensification—preferably synergistic intensification—of the sweet taste of the substance(s) (b) or (d), and (b) for masking or reducing the unpleasant taste impression of the unpleasant-tasting substance(s) (c) or (d).

A further aspect related to the present invention, therefore concerns the use (a) of hesperetin dihydrochalcone (I), or a salt of the hesperetin dihydrochalcone (I) or a mixture comprising or consisting of a plurality of salts of the hesperetin dihydrochalcone (I), or a mixture comprising or consisting of hesperetin dihydrochalcone (I) and a salt or a plurality of salts of the hesperetin dihydrochalcone (I), as described in each case above, in a mixture comprising at least one or a plurality of the substances selected from the group consisting of substance(s) (c) and (d) or mixtures thereof, wherein substance(s) (c) means one or more unpleasant-tasting substances, preferably bitter-, sour-, and/or astringent-tasting substances, in particular bitter-tasting substances substance(s) (d) means one or more both sweet-tasting substances and unpleasant-tasting substances, in particular bitter-tasting substances; and/or one or more sweet-tasting substances (b), and/or one or more substances having a taste impression selected from the group consisting of cooling, umami, fruity and spicy taste impression or mixtures thereof, (a) for the intensification—preferably synergistic intensification—of the sweet taste of the substance(s) (b) or (d), and/or (b) for masking or reducing the unpleasant taste impression of the unpleasant-tasting substance(s) (c) or (d), in particular a bitter tasting impression, and/or (c) for modulating taste impression selected from the group consisting of cooling, sweet, umami, fruity and spicy taste impression or mixtures thereof.

Thus, it was surprisingly found that the use of hesperetin dihydrochalcone (I) causes an improvement of the taste profile in the above mentioned mixtures, in particular regarding a faster and better perception of cooling, sweet, umami, fruity and spicy notes.

A further aspect related to the present invention, therefore concerns the use (a) of hesperetin dihydrochalcone (I), or a salt of the hesperetin dihydrochalcone (I) or a mixture comprising or consisting of a plurality of salts of the hesperetin dihydrochalcone (I)

or a mixture comprising or consisting of hesperetin dihydrochalcone (I) and a salt or a plurality of salts of the hesperetin dihydrochalcone (I), as described in each case above, in a mixture comprising at least one or a plurality of the substances selected from the group consisting of substance(s) (c) and (d) or mixtures thereof, wherein substance(s) (c) means one or more unpleasant-tasting substances, preferably bitter-, sour-, and/or astringent-tasting substances, in particular bitter-tasting substances substance(s) (d) means one or more both sweet-tasting substances and unpleasant-tasting substances, in particular bitter-tasting substances; and/or one or more sweet-tasting substances (b), and one or more substances having a taste impression selected from the group consisting of cooling, umami, fruity and spicy taste impression or mixtures thereof, (a) for the intensification—preferably synergistic intensification—of the sweet taste of the substance(s) (b) or (d), and (b) for masking or reducing the unpleasant taste impression of the unpleasant-tasting substance(s) (c) or (d), in particular a bitter tasting impression, and (c) for modulating taste impression selected from the group consisting of cooling, sweet, umami, fruity and spicy taste impression or mixtures thereof.

A further aspect related to the present invention, therefore concerns the use (a) of hesperetin dihydrochalcone (I) or a salt of the hesperetin dihydrochalcone (I) or a mixture comprising or consisting of a plurality of salts of the hesperetin dihydrochalcone (I), or a mixture comprising or consisting of hesperetin dihydrochalcone (I) and a salt or a plurality of salts of the hesperetin dihydrochalcone (I), as described in each case above, in a mixture comprising at least one or a plurality of the substances selected from the group consisting of substance(s) (c) and (d) or mixtures thereof, wherein substance(s) (c) means one or more unpleasant-tasting substances, preferably bitter-, sour-, and/or astringent-tasting substances, in particular bitter-tasting substances substance(s) (d) means one or more both sweet-tasting substances and unpleasant-tasting substances, in particular bitter-tasting substances; and one or more sweet-tasting substances (b), and one or more substances having a taste impression selected from the group consisting of cooling, umami, fruity and spicy taste impression or mixtures thereof, (a) for the intensification—preferably synergistic intensification—of the sweet taste of the substance(s) (b) or (d), and (b) for masking or reducing the unpleasant taste impression of the unpleasant-tasting substance(s) (c) or (d), in particular a bitter tasting impression, and (c) for modulating taste impression selected from the group consisting of cooling, sweet, umami, fruity and spicy taste impression or mixtures thereof.

That stated above concerning hesperetin dihydrochalcone (I), its salts or mixtures comprising or consisting of a plurality of salts of the hesperetin dihydrochalcone (I) or mixtures comprising or consisting of hesperetin dihydrochalcone (I) and a salt or a plurality of salts of the hesperetin dihydrochalcone (I) applies here accordingly.

Preferably the mixture is an aroma composition or preparation selected from the group consisting of preparations serving for nutrition, as food supplements, for oral care or for pleasure, as cosmetic preparations, in particular for application in the region of the head, pharmaceutical preparations intended to be taken orally, flavouring mixtures for use in one of the abovementioned preparations, or semi-finished products for manufacturing one of the preparations mentioned above.

Sweet-tasting substances for the purposes of the present invention are in particular:

sweet-tasting carbohydrates
(e.g. sucrose, trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde), sweet-tasting sugar alcohols
(e.g. erythritol, threitol, arabitol, ribitol, xylitol, sorbitol, mannitol, dulcitol, lactitol), sweet-tasting proteins (e.g. miraculin, pentadin, monellin, thaumatin, curculin, brazzein), sweeteners (e.g. magap, sodium cyclamate, acesulfame K, neohesperidine dihydrochalcone, naringin hydrochalcone, saccharin, saccharin sodium salt, aspartame, superaspartame, neotame, sucralose, lugduname, carrelame, sucrononate, sucrooctate or naturally occurring sweeteners such as miraculin, curculin, monellin, mabinlin, thaumatin, curculin, brazzein, pentadin, D-phenylalanine, D-tryptophan, or extracts or fractions derived from natural sources containing these amino acids and/or proteins, neohesperidin dihydrochalcone, steviolgylcosides, steviosides, steviolbioside, rebaudiosides, rebaudioside A, rebaudioside B, rebaudioside C, rebaudioside D, rebaudioside E, rebaudioside F, rebaudioside G, rebaudioside H, rebaudioside I, rebaudioside O, rebaudioside M, rebaudioside N, rebaudioside V, rebaudioside W, rebaudioside X, rebaudioside Z, rebaudioside KA, dulcoside A, dulcoside B, rubusoside, suavioside A, suavioside B, suavioside G, suavioside H, suavioside I, suavioside J, baiyunoside 1, baiyunoside 2, phlomisoside 1, phlomisoside 2, phlomisoside 3, phlomisoside 4, abrusoside A, abrusoside B, abrusoside C, abrusoside D, cyclocaryoside A, cyclocaryoside I, oslandin, polypodoside A, strogin 1, strogin 2, strogin 4, selligueanin A, dihydroquercetin-3-acetate, perillartine, telosmoside $A_{15}$, periandrin I-V, pterocaryoside, cyclocaryoside, mukurozioside, trans-anethole, trans-cinnamaldehyde, bryosides, bryonosides, bryonodulcosides, carnosiflosides, scandenosides, gypenosides, trilobtain, phloridzin, dihydroflavanols, hematoxylin, cyanin, chlorogenic acid, albiziasaponin, telosmosides, gaudichaudioside, mogrosides, hernandulcines, monatin, glycyrrhetin acid and derivatives and salts thereof, phyllodulcin, balansin A, and balansin B).

Apart from the sweet primary taste, sweet-tasting substances can have one or more further test impressions (and/or olfactory impressions), in particular a non-sweet aftertaste impression. Here primary taste means the taste impression that is made while substance is in direct contact with the mucous lining of the oral cavity, in particular with the tongue (as a rule lasting from a few seconds to a few minutes). Aftertaste here means the taste impression that is left once the oral cavity has been emptied by swallowing and/or disgorging and which through the adhesion of residues of the substance remains in place and can stay there for between a few minutes and a few hours.

In particular sweet-tasting substances, as mentioned in the introduction, can also have unpleasant, in particular bitter, taste impressions. In order to influence the taste impressions of such both sweet- and unpleasant-, in particular bitter-, tasting substances (d) hesperetin dihydrochalcone (I) or a salt of the hesperetin dihydrochalcone (I) or a mixture comprising or consisting of a plurality of salts of hesperetin dihydrochalcone (I) or a mixture comprising or consisting of hesperetin dihydrochalcone (I) and a salt or a plurality of salts of the hesperetin dihydrochalcone (I) are preferably used. The presence of other taste impressions of a substance, but also the intensity of the primary taste itself can, for example, vary according to the concentration of the substance, the temperature, the pH and/or the other substances present apart from this substance.

Thus for example when dealing with stevioside or rebaudioside A or another steviolglycoside (as described above), it is the case that the sweetening power of these will be dependent upon various factors such as temperature, pH, concentration and the product to be sweetened. In particular according to the concentration (at high concentrations, especially at more than 50 ppm, particularly at 50-2000 ppm, quite particularly at 100 ppm-1000 ppm) a bitter aftertaste occurs, which as a rule is undesired. In the context of the present invention stevioside or rebaudioside A are particularly preferably both sweet and bitter tasting substances (d).

Unpleasant-, in particular bitter-, tasting substances with additional sweet taste impression are for the purposes of this invention in turn classified as both sweet- and unpleasant-tasting substances.

In the context of the present invention the respective unpleasant taste impressions are similarly to be assigned corresponding taste impressions determined by an aftertaste.

Unpleasant-tasting substances for the purposes of this invention are therefore:

substances with a bitter, sour, astringent, cardboardy, chalky, dusty, dry, floury, rancid or metallic taste, and
substances with a corresponding (possibly long-lasting) aftertaste.

Here a bitter taste impression is often associated with the sour, astringent, cardboardy, chalky, dusty, dry, floury, rancid and/or metallic taste impressions.

Substances (c), which taste unpleasant, i.e. bitter, sour, astringent, cardboardy, chalky, dusty, dry, floury, rancid or metallic taste, are for example:

Xanthine alkaloids, xanthines (caffeine, theobromine, theophylline), alkaloids (quinine, Chininhydrochloride, brucine, strychnine, nicotine), phenolic glycosides (e.g. salicin, arbutin), flavonoid glycosides (e.g. hesperidine, naringin), chalcones or chalcone glycosides, hydrolysable tannins (gallic or ellagic acid esters of carbohydrates, e.g. pentagalloyl-glucose), non-hydrolysable tannins (optionally galloylated catechols or epicatechols and oligomers thereof, e.g. proanthyocyanidines or procyanidines, thearubigin), flavones (e.g. quercertin, taxifolin, myricetin), other polyphenols (gamma-oryzanol, coffeic acid or esters thereof), terpenoid bitter substances (e.g. limonoids such as limonine or nomilin from citrus fruits, lupolones and humulones from hops, iridoids, secoiridoids), absinthin from wormwood, amarogentin from gentian, metal salts (potassium chloride, sodium sulfate, magnesium salts, iron salts, aluminum salts, zinc salts), pharmaceutical active ingredients (e.g. fluoroquinolone antibiotics, beta-lactam antibiotics, ambroxol, propylthiouracil [PROP], aspirin (acetyl salicylic acid), salicin, paracetamol (acetaminophene), ibuprofen, naproxen, ambroxol, guafenesin, omeprazole, pantoprazole, dextromorphane, or quinine), vitamins (for example vitamin H, vitamins from the B group, such as vitamin B1, B2, B6, B12, niacin, pantothenic acid), denatonium benzoate or other denatonium salts, sucralose octaacetate, urea, unsaturated fatty acids, in particular unsaturated fatty acids in emulsions, amino acids (e.g. leucine, isoleucine, valine, tryptophan, proline, histidine, tyrosine, lysine or phenylalanine, in particular the respective L-enantiomers of leucine, isoleucine, valine, tryptophane, proline, histidine, tyrosine, lysine or phenylalanine), peptides (in particular peptides having an amino acid from the group L-leucine, L-isoleucine, L-valine, L-tryptophane, L-proline or L-phenylalanine at the N- or C-terminus).

Substances, in particular aromatic substances or flavourings, often have a bitter, sour, astringent, cardboardy, chalky, dusty, dry, floury, rancid and/or metallic aftertaste, though they have a not unpleasant (primary) taste for the purposes of the above definition (i.e. e.g. sweet, salty, spicy, sour, etc.) and/or smell. These aromatic substances or flavourings with an unpleasant (after-) taste are unpleasant-tasting substances (c) or in particular (where they have a sweet (primary) taste) both sweet- and also unpleasant-tasting substances (d) for the purposes of this invention. These aromatic substances or flavourings are in particular selected from the group of sweeteners (as described above) or sugar substitutes, i.e. these aromatic substances or flavourings have a sweet (primary) taste. Specific examples of such aromatic substances or flavourings are aspartame, neotame, superaspartame, saccharin, sucralose, tagatose, monellin, stevioside, rebaudioside, above all rebaudioside A, mogroside, in particular mogroside V, thaumatin, miraculin, glycyrrhizin, glycyrrhetinic acid or derivatives thereof, cyclamates or the pharmaceutically acceptable salts of the above-mentioned compounds. The aromatic substances or flavourings are preferred both sweet- and unpleasant/bitter-tasting substances (d) for the applications according to the invention. The unpleasant taste impression of these substances, in particular a bitter taste impression of these substances, in a use according to the invention (as described above) can be particularly effectively masked or reduced.

Further unpleasant-tasting substances (c) or both sweet- and unpleasant-tasting substances (d), the unpleasant (after) taste of which according to the invention can be advantageously masked or reduced, are for example aromatic substances which have a sweet taste impression and are preferably selected from the group consisting of: vanillin, ethylvanillin, 2-hydroxy-4-methoxybenzaldehyde, ethylvanillin isobutyrate (=3-ethoxy-4-isobutyryloxybenzaldehyde), Furaneol® (2,5-dimethyl-4-hydroxy-3(2H)-furanone) and derivatives thereof (e.g. homofuraneol, 2-ethyl-4-hydroxy-5-methyl-3(2H)-furanone), homofuronol (2-ethyl-5-methyl-4-hydroxy-3(2H)-fura none and 5-ethyl-2-methyl-4-hydroxy-3(2H)furanone), maltol and derivatives thereof (e.g. ethylmaltol), coumarin and derivatives thereof, gamma-lactones (e.g. gamma-undecalactone, gamma-nonalactone), delta-lactones (e.g. 4-methyl-delta-lactone, massoilactone, delta-decalactone, tuberolactone), methyl sorbate, divanillin, 4-hydroxy-2(or 5)-ethyl-5(or 2)-methyl-3 (2H)furanone, 2-hydroxy-3-methyl-2-cyclopentenones, 3-hydroxy-4,5-dimethyl-2(5H)-furanone, fruit esters and fruit lactones (e.g. n-butyl acetate, isoamyl acetate, ethyl propionate, ethyl butyrate, n-butyl butyrate, isoamyl butyrate, ethyl 3-methyl-butyrate, ethyl n-hexanoate, allyl n-hexanoate, n-butyl n-hexanoate, ethyl n-octanoate, ethyl-3-methyl-3-phenylglycidate, ethyl-2-trans-4-cis-decadienoate), 4-(p-hydroxyphenyl)-2-butanone, 1,1-dimethoxy-2,2, 5-trimethyl-4-hexane, 2,6-dimethyl-5-hepten-1-al and phenylacetaldehyde.

Particular preference is for a use according to the invention (as described above), wherein the bitter-tasting substance (c) or the both sweet- and bitter-tasting substance (d), is selected from the group consisting of steviolglycosides, in particular stevioside and rebaudiosides. The bitter-tasting substance (c) or the both sweet- and bitter-tasting substance (d) is preferably selected from the group consisting of rebaudioside A, rubusoside, dulcoside, mogroside, phyllodulcin, glycyrrhetin acid or extracts of *Stevia* ssp. (in particular *Stevia rebaudiana*), Luo Han Guo, *Rubus suavissimus, Hydrangea dulcis, Mycetia balansae* or *Glycyrrhyza glabra*.

Through the use according to the invention of hesperetin dihydrochalcone (I) or a salt of the hesperetin dihydrochalcone (I) or a mixture comprising or consisting of a plurality of salts of the hesperetin dihydrochalcone (I) or a mixture comprising or consisting of hesperetin dihydrochalcone (I) and a salt or a plurality of salts of the hesperetin dihydrochalcone (I) the overall content of sweet-tasting substances (e.g. in the preparations intended for nutrition or pleasure) can be advantageously reduced, without reducing the overall sweet taste impression. This is not only important on health grounds, but also in terms of the taste features. In particular, a sweet-(and at high concentrations also bitter-) tasting substance such as for example stevioside can be used in combination with hesperetin dihydrochalcone (I) or a salt of the hesperetin dihydrochalcone (I) or a mixture comprising or consisting of a plurality of salts of the hesperetin dihydrochalcone (I) or a mixture comprising or consisting of hesperetin dihydrochalcone (I) and a salt or a plurality of salts of the hesperetin dihydrochalcone (I) advantageously (maintaining the sweet taste impressions) in concentrations that are small enough so that no or at least only a reduced bitter (after)taste of the both sweet- and bitter-tasting substance such as for example of stevioside is noticed. In addition, the bitter taste impression (of the both sweet- and bitter-tasting substance) can be advantageously masked or at least (further) reduced by a preferred use according to the invention (as described above).

Various studies with *Stevia* extracts (Yamada A. et al. (1985): Chronic toxicity study of dietary *Stevia* extracts in F344 rats. In: *J. Food Hyg. Soc. Japan*. Bd. 26, S. 169-183; Melis, M. S. (1999): Effects of chronic administration of *Stevia rebaudiana* on fertility in rats. In: *J. Ethnopharmacol*. Bd. 67, S. 157-161) have reported on the effects on the human reproduction system, such as for example reduced spermatogenesis, lower weight of the seminal vesicles and interstitial cell proliferation in the testicles. It is also known that the leaves of *Stevia rebaudiana* have been used by Paraguayan Indians in tea as a male contraceptive.

In addition, a reduction in the quantity of *Stevia* extract or steviol glycosides required can also result in cost savings on top of the advantages already mentioned.

In a use according to the invention it can be advantageous if not all unpleasant- or bitter-tasting nuances are (completely) masked, since in some circumstances these can also be desirable.

In a use according to the invention (as described above) it is also a case preferably of a preparation intended as an oral pharmaceutical, as a cosmetic, for nutrition, as a food supplement, for oral care or pleasure. Preparations according to the invention and their preferred embodiments are described further on.

Therefore, it was a further object of the present invention to provide an aroma composition comprising a compound of formula (I) or a salt of the compound of formula (I) or a mixture comprising or consisting of a plurality of salts of the compound of formula (I), or a mixture comprising or consisting the compound of formula (I) and a salt or a plurality of salts of the compound of formula (I).

In a particularly preferred embodiment according to the present invention, the aroma composition comprises two or more different salts of the hesperetin dihydrochalcone (I) or hesperetin dihydrochalcone (I) and one or a plurality of different salts of hesperetin dihydrochalcone (I), as described above, wherein the counter cation(s) of the, one, a plurality of or all the salts of the hesperetin dihydrochalcone (I) is or are selected from the group consisting of $Na^+$, $K^+$, $NH_4^+$, $Ca^{2+}$, $Mg^{2+}$, $Al^{3+}$ and $Zn^{2+}$, particularly preferred selected from the group consisting of $Na^+$ and $K^+$.

In a preferred embodiment, the aroma composition according to the present invention comprises a compound of formula (I) or a salt of the compound of formula (I) or a mixture comprising or consisting of a plurality of salts of the compound of formula (I), or a mixture comprising or consisting the compound of formula (I) and a salt or a plurality of salts of the compound of formula (I) in an amount in the range 0.001-10% based on the total weight of the aroma composition, preferably in the range 0.002-5% based on the total weight of the aroma composition, more preferably in the range 0.05-2% based on the total weight of the aroma composition, and particularly preferred in the range 0.05-1% based on the total weight of the aroma composition.

A further object for the present invention was to provide an aroma composition, with which sweet taste impression of a sweet-tasting substance the strength of taste impressions of sweet-tasting, and/or unpleasant-, in particular bitter-tasting and/or both sweet- and unpleasant-, in particular bitter-, tasting substances is influenced, in particular the sweet taste impression of a sweet-tasting substance, is intensified, preferably synergistically intensified and—where the sweet-tasting substance has a bitter off- and/or aftertaste—preferably in addition the bitter taste impression is masked or reduced. It is similarly preferred that the strength of an unpleasant (in particular bitter) taste impression of substances or mixtures of substances without a sweet taste is masked or reduced.

Consequently hesperetin dihydrochalcone (I) or a salt of the hesperetin dihydrochalcone (I) or a mixture comprising or consisting of a plurality of salts of the hesperetin dihydrochalcone (I) or a mixture comprising or consisting hesperetin dihydrochalcone (I) and a salt or a plurality of salts of hesperetin dihydrochalcone (I) according to a further aspect of this invention in an aroma composition is used for intensification—preferably synergistic intensification—of the sweet taste of a sweet-tasting substance and for masking or reducing or supressing a bitter taste impression of a bitter-tasting substance. Such an aroma composition is advantageously particularly well-suited to intensification—preferably synergistic intensification—of a sweet and/or for masking or reducing a bitter taste impression of a both sweet- and bitter-tasting substance.

This invention also concerns an aroma composition comprising or consisting of the following components:

(a) a compound of formula (I) or a salt of the compound of formula (I) or a mixture comprising or consisting of a plurality of salts of the compound of formula (I), or a mixture comprising or consisting the compound of formula (I) and a salt or a plurality of salts of the compound of formula (I); and at least one or a plurality of the substances selected from the group consisting of substance(s) (c) and (d) or mixtures thereof, wherein substance(s) (c) means one or more unpleasant-tasting substances, preferably bitter-, sour-, and/or astringent-tasting substances, in particular bitter-tasting substances substance(s) (d) means one or more both sweet-tasting substances and unpleasant-tasting substances, in particular bitter-tasting substances; and/or (b) one or more sweet-tasting substances; and optionally comprises:

(e) one or more substances to mask or reduce an unpleasant taste impression, in particular a bitter taste impression, and/or (f) one or more further substances for intensifying a sweet taste impression, and/or (g) one or more substances to mask or reduce a metallic, chalky, sour, or astringent taste impression, and/or (h) one or more substances having a taste impression selected from the group consisting of cooling, umami, fruity and spicy taste impression or mixtures thereof;

wherein components (b)-(h) do not comprise hesperetin dihydrochalcone (I) or a salt of hesperetin dihydrochalcone (I).

This invention also concerns an aroma composition comprising or consisting of the following components:

(a) a compound of formula (I) or a salt of the compound of formula (I) or a mixture comprising or consisting of a plurality of salts of the compound of formula (I), or a mixture comprising or consisting the compound of formula (I) and a salt or a plurality of salts of the compound of formula (I);

and at least one or a plurality of the substances selected from the group consisting of substance(s) (c) and (d) or mixtures thereof, wherein substance(s) (c) means one or more unpleasant-tasting substances, preferably bitter-, sour-, and/or astringent-tasting substances, in particular bitter-tasting substances substance(s) (d) means one or more both sweet-tasting substances and unpleasant-tasting substances, in particular bitter-tasting substances; and/or (b) one or more sweet-tasting substances; and optionally comprises:

(e) one or more substances to mask or reduce an unpleasant taste impression, in particular a bitter taste impression, and/or (f) one or more further substances for intensifying a sweet taste impression, and/or (g) one or more substances to mask or reduce a metallic, chalky, sour, or astringent taste impression, and/or (h) one or more substances having a taste impression selected from the group consisting of cooling, umami, fruity and spicy taste impression or mixtures thereof;

wherein components (b)-(h) do not comprise hesperetin dihydrochalcone (I) or a salt of hesperetin dihydrochalcone (I).

wherein the total amount of component (a) is sufficient to enhance—preferably synergistically—the sweet taste of the sweet-tasting substance, in comparison to an otherwise equivalent composition without hesperetin dihydrochalcone (I) and/or salt(s) thereof, and wherein the total amount of hesperetin dihydrochalcone (I) and/or salt(s) thereof is sufficient to reduce and/or mask the unpleasant taste of the bitter-, sour-, and/or astringent-tasting substance(s).

This invention also concerns an aroma composition comprising or consisting of the following components:
(a) a compound of formula (I) or a salt of the compound of formula (I) or a mixture comprising or consisting of a plurality of salts of the compound of formula (I), or a mixture comprising or consisting the compound of formula (I) and a salt or a plurality of salts of the compound of formula (I);
and at least one or a plurality of the substances selected from the group consisting of substance(s) (c) and (d) or mixtures thereof, wherein
   substance(s) (c) means one or more unpleasant-tasting substances, preferably bitter-, sour-, and/or astringent-tasting substances, in particular bitter-tasting substances
   substance(s) (d) means one or more both sweet-tasting substances and unpleasant-tasting substances, in particular bitter-tasting substances; and/or
(b) one or more sweet-tasting substances; and optionally comprises:
(e) one or more substances to mask or reduce an unpleasant taste impression, in particular a bitter taste impression, and/or
(f) one or more further substances for intensifying a sweet taste impression, and/or
(g) one or more substances to mask or reduce a metallic, chalky, sour, or astringent taste impression, and/or
(h) one or more substances having a taste impression selected from the group consisting of cooling, umami, fruity and spicy taste impression or mixtures thereof;
wherein components (b)-(h) do not comprise hesperetin dihydrochalcone (I) or a salt of hesperetin dihydrochalcone (I).
wherein the total amount of component (a) is sufficient to enhance—preferably synergistically—the sweet taste of the sweet-tasting substance, in comparison to an otherwise equivalent composition without hesperetin dihydrochalcone (I) and/or salt(s) thereof, and
wherein the total amount of hesperetin dihydrochalcone (I) and/or salt(s) thereof is sufficient to reduce and/or mask the unpleasant taste of the bitter-, sour-, and/or astringent-tasting substance(s), and
wherein the total amount of hesperetin dihydrochalcone (I) and/or salt(s) thereof is sufficient to modulate the taste impressions of the components (h).

Further the present invention also concerns an aroma composition comprising or consisting of the following components:
(a) a compound of formula (I) or a salt of the compound of formula (I) or a mixture comprising or consisting of a plurality of salts of the compound of formula (I), or a mixture comprising or consisting the compound of formula (I) and a salt or a plurality of salts of the compound of formula (I);
and at least one or a plurality of the substances selected from the group consisting of substance(s) (c) and (d) or mixtures thereof, wherein
   substance(s) (c) means one or more unpleasant-tasting substances, preferably bitter-, sour-, and/or astringent-tasting substances, in particular bitter-tasting substances
   substance(s) (d) means one or more both sweet-tasting substances and unpleasant-tasting substances, in particular bitter-tasting substances; and
(e) one or more substances to mask or reduce an unpleasant taste impression, in particular a bitter taste impression; and optionally comprises:
(b) one or more sweet-tasting substances; and/or
(f) one or more further substances for intensifying a sweet taste impression, particularly preferred selected from the group consisting of hesperetin, phloretin, rubusoside, fermented *rubus* extract according to EP 2,954,785-A1, naringenin, balansin A, Balansin B and phyllodulcin, and/or
(g) one or more substances to mask or reduce a metallic, chalky, sour, or astringent taste impression, and/or
(h) one or more substances having a taste impression selected from the group consisting of cooling, umami, fruity and spicy taste impression or mixtures thereof;
wherein components (b)-(h) do not comprise hesperetin dihydrochalcone (I) or a salt of hesperetin dihydrochalcone (I).

Particular preference is for an aroma composition comprising or consisting of the following components:
(a) a compound of formula (I) or a salt of the compound of formula (I) or a mixture comprising or consisting of a plurality of salts of the compound of formula (I), or a mixture comprising or consisting the compound of formula (I) and a salt or a plurality of salts of the compound of formula (I);
and at least one or a plurality of the substances selected from the group consisting of substance(s) (c) and (d) or mixtures thereof, wherein
   substance(s) (c) means one or more unpleasant-tasting substances, preferably bitter-, sour-, and/or astringent-tasting substances, in particular bitter-tasting substances
   substance(s) (d) means one or more both sweet-tasting substances and unpleasant-tasting substances, in particular bitter-tasting substances; and
(e) at least one of the substances selected from the group consisting of homoeriodictyol or its sodium salts, eriodictyol, matairesinol, lariciresinol, naringenin, phloretin, 5-hydroxy-4-(4-hydroxy-3-methoxyphenyl)-7-methoxychroman-2-one, 5,7-dihydroxy-4-(4-hydroxyphenyl)chroman-2-one, 5,7-dihydroxy-4-(4-hydroxy-3-methoxyphenyl)chroman-2-one and 2,4-dihydroxybenzoic acid vanillyl amide and optionally more substances to mask or reduce an unpleasant taste impression, in particular a bitter taste impression; and optionally comprises:
(b) one or more sweet-tasting substances; and/or
(f) one or more further substances for intensifying a sweet taste impression, particularly preferred selected from the group consisting of hesperetin, phloretin, rubusoside, fermented *rubus* extract according to EP 2,954,785-A1, naringenin, balansin A, Balansin B and phyllodulcin, and/or
(g) one or more substances to mask or reduce a metallic, chalky, sour, or astringent taste impression, and/or
(h) one or more substances having a taste impression selected from the group consisting of cooling, umami, fruity and spicy taste impression or mixtures thereof;
wherein components (b)-(h) do not comprise hesperetin dihydrochalcone (I) or a salt of hesperetin dihydrochalcone (I).

Further, particular preference is for an aroma composition comprising or consisting of the following components:
(a) a compound of formula (I) or a salt of the compound of formula (I) or a mixture comprising or consisting of a plurality of salts of the compound of formula (I), or a mixture comprising or consisting the compound of formula (I) and a salt or a plurality of salts of the compound of formula (I); and at least one or a plurality of the substances selected from the group consisting of substance(s) (c) and (d) or mixtures thereof, wherein substance(s) (c) means one or more unpleasant-tasting substances, preferably bitter-, sour-, and/or astringent-tasting substances, in particular bitter-tasting substances substance(s) (d) means one or more both sweet-tasting substances and unpleasant-tasting substances, in particular bitter-tasting substances; and (e) homoeriodictyol or its sodium salts, and optionally at least one of the substances selected from the group consisting of eriodictyol, matairesinol, lariciresinol, naringenin, phloretin, 5-hydroxy-4-(4-hydroxy-3-methoxyphenyl)-7-methoxychroman-2-one, 5,7-dihydroxy-4-(4-hydroxyphenyl)chroman-2-one, 5,7-dihydroxy-4-(4-hydroxy-3-methoxyphenyl)chroman-2-one, or 2,4-dihydroxybenzoic acid vanillyl amide and optionally more substances to mask or reduce an unpleasant taste impression, in particular a bitter taste impression; and optionally comprises:

(b) one or more sweet-tasting substances; and/or (f) one or more further substances for intensifying a sweet taste impression, particularly preferred selected from the group consisting of hesperetin, phloretin, rubusoside, fermented *rubus* extract according to EP 2,954,785-A1, naringenin, balansin A, Balansin B and phyllodulcin, and/or (g) one or more substances to mask or reduce a metallic, chalky, sour, or astringent taste impression, and/or (h) one or more substances having a taste impression selected from the group consisting of cooling, umami, fruity and spicy taste impression or mixtures thereof;

wherein components (b)-(h) do not comprise hesperetin dihydrochalcone (I) or a salt of hesperetin dihydrochalcone (I).

Consequently this invention also concerns an aroma composition comprising or consisting of the following components:

(a) a compound of formula (I) or a salt of the compound of formula (I) or a mixture comprising or consisting of a plurality of salts of the compound of formula (I), or a mixture comprising or consisting the compound of formula (I) and a salt or a plurality of salts of the compound of formula (I); and at least one or a plurality of the substances selected from the group consisting of substance(s) (c) and (d) or mixtures thereof, wherein substance(s) (c) means one or more unpleasant-tasting substances, preferably bitter-, sour-, and/or astringent-tasting substances, in particular bitter-tasting substances substance(s) (d) means one or more both sweet-tasting substances and unpleasant-tasting substances, in particular bitter-tasting substances; and/or (b) one or more sweet-tasting substances; and optionally comprises:

(e) one or more substances to mask or reduce an unpleasant taste impression, in particular a bitter taste impression, and/or (f) one or more further substances for intensifying a sweet taste impression, particularly preferred selected from the group consisting of hesperetin, phloretin, rubusoside, fermented *rubus* extract according to EP 2,954,785-A1, naringenin, balansin A, Balansin B and phyllodulcin, and/or (g) one or more substances to mask or reduce a metallic, chalky, sour, or astringent taste impression, and/or (h) one or more substances having a taste impression selected from the group consisting of cooling, umami, fruity and spicy taste impression or mixtures thereof;

wherein components (b)-(h) do not comprise hesperetin dihydrochalcone (I) or a salt of hesperetin dihydrochalcone (I) and, wherein the total amount of component (a) is sufficient to enhance—preferably synergistically—the sweet taste of the sweet-tasting substance, in comparison to an otherwise equivalent composition without hesperetin dihydrochalcone (I) and/or salt(s) thereof, and wherein the total amount of hesperetin dihydrochalcone (I) and/or salt(s) thereof is sufficient to reduce and/or mask the unpleasant taste of the bitter-, sour-, and/or astringent-tasting substance(s), and wherein the total amount of hesperetin dihydrochalcone (I) and/or salt(s) thereof is sufficient to modulate the taste impressions of the components (h).

Therefore this invention also concerns an aroma composition comprising or consisting of the following components:

(a) a compound of formula (I) or a salt of the compound of formula (I) or a mixture comprising or consisting of a plurality of salts of the compound of formula (I), or a mixture comprising or consisting the compound of formula (I) and a salt or a plurality of salts of the compound of formula (I); and at least one or a plurality of the substances selected from the group consisting of substance(s) (c) and (d) or mixtures thereof, wherein substance(s) (c) means one or more unpleasant-tasting substances, preferably bitter-, sour-, and/or astringent-tasting substances, in particular bitter-tasting substances substance(s) (d) means one or more both sweet-tasting substances and unpleasant-tasting substances, in particular bitter-tasting substances; and (b) one or more sweet-tasting substances; and further comprises:

(e) one or more substances to mask or reduce an unpleasant taste impression, in particular a bitter taste impression, and/or (f) one or more further substances for intensifying a sweet taste impression, particularly preferred selected from the group consisting of hesperetin, phloretin, rubusoside, fermented *rubus* extract according to EP 2,954,785-A1, naringenin, balansin A, Balansin B and phyllodulcin, and (g) one or more substances to mask or reduce a metallic, chalky, sour, or astringent taste impression, and (h) one or more substances having a taste impression selected from the group consisting of cooling, umami, fruity and spicy taste impression or mixtures thereof;

wherein components (b)-(h) do not comprise hesperetin dihydrochalcone (I) or a salt of hesperetin dihydrochalcone (I) and, wherein the total amount of component (a) is sufficient to enhance—preferably synergistically—the sweet taste of the sweet-tasting substance, in comparison to an otherwise equivalent composition without hesperetin dihydrochalcone (I) and/or salt(s) thereof, and wherein the total amount of hesperetin dihydrochalcone (I) and/or salt(s) thereof is sufficient to reduce and/or mask the unpleasant taste of the bitter-, sour-, and/or astringent-tasting substance(s), and wherein the total amount of hesperetin dihydrochalcone (I) and/or salt(s) thereof is sufficient to modulate the taste impressions of the components (h).

Further the present invention also concerns an aroma composition comprising or consisting of the following components:
(a) a compound of formula (I) or a salt of the compound of formula (I) or a mixture comprising or consisting of a plurality of salts of the compound of formula (I), or a mixture comprising or consisting the compound of formula (I) and a salt or a plurality of salts of the compound of formula (I); and at least one or a plurality of the substances selected from the group consisting of substance(s) (c) and (d) or mixtures thereof, wherein
substance(s) (c) means one or more unpleasant-tasting substances, preferably bitter-, sour-, and/or astringent-tasting substances, in particular bitter-tasting substances
substance(s) (d) means one or more both sweet-tasting substances and unpleasant-tasting substances, in particular bitter-tasting substances; and
(e) one or more substances to mask or reduce an unpleasant taste impression, in particular a bitter taste impression; and optionally comprises:
(b) one or more sweet-tasting substances; and/or
(f) one or more further substances for intensifying a sweet taste impression, particularly preferred selected from the group consisting of hesperetin, phloretin, rubusoside, fermented *rubus* extract according to EP 2,954,785-A1, naringenin, balansin A, Balansin B and phyllodulcin, and/or
(g) one or more substances to mask or reduce a metallic, chalky, sour, or astringent taste impression, and/or
(h) one or more substances having a taste impression selected from the group consisting of cooling, umami, fruity and spicy taste impression or mixtures thereof;
wherein components (b)-(h) do not comprise hesperetin dihydrochalcone (I) or a salt of hesperetin dihydrochalcone (I) and,
wherein the total amount of component (a) is sufficient to enhance—preferably synergistically—the sweet taste of the sweet-tasting substance, in comparison to an otherwise equivalent composition without hesperetin dihydrochalcone (I) and/or salt(s) thereof, and
wherein the total amount of hesperetin dihydrochalcone (I) and/or salt(s) thereof is sufficient to reduce and/or mask the unpleasant taste of the bitter-, sour-, and/or astringent-tasting substance(s), and
wherein the total amount of hesperetin dihydrochalcone (I) and/or salt(s) thereof is sufficient to modulate the taste impressions of the components (h).

Particular preference is for an aroma composition comprising or consisting of the following components:
(a) a compound of formula (I) or a salt of the compound of formula (I) or a mixture comprising or consisting of a plurality of salts of the compound of formula (I), or a mixture comprising or consisting the compound of formula (I) and a salt or a plurality of salts of the compound of formula (I); and at least one or a plurality of the substances selected from the group consisting of substance(s) (c) and (d) or mixtures thereof, wherein
substance(s) (c) means one or more unpleasant-tasting substances, preferably bitter-, sour-, and/or astringent-tasting substances, in particular bitter-tasting substances
substance(s) (d) means one or more both sweet-tasting substances and unpleasant-tasting substances, in particular bitter-tasting substances; and
(e) at least one of the substances selected from the group consisting of homoeriodictyol or its sodium salts, eriodictyol, matairesinol, lariciresinol, naringenin, phloretin, 5-hydroxy-4-(4-hydroxy-3-methoxyphenyl)-7-methoxychroman-2-one, 5,7-dihydroxy-4-(4-hydroxyphenyl)chroman-2-one, 5,7-dihydroxy-4-(4-hydroxy-3-methoxyphenyl)chroman-2-one and 2,4-dihydroxybenzoic acid vanillyl amide and optionally more substances to mask or reduce an unpleasant taste impression, in particular a bitter taste impression; and optionally comprises:
(b) one or more sweet-tasting substances; and/or
(f) one or more further substances for intensifying a sweet taste impression, particularly preferred selected from the group consisting of hesperetin, phloretin, rubusoside, fermented *rubus* extract according to EP 2,954,785-A1, naringenin, balansin A, Balansin B and phyllodulcin, and/or
(g) one or more substances to mask or reduce a metallic, chalky, sour, or astringent taste impression, and/or
(h) one or more substances having a taste impression selected from the group consisting of cooling, umami, fruity and spicy taste impression or mixtures thereof;
wherein components (b)-(h) do not comprise hesperetin dihydrochalcone (I) or a salt of hesperetin dihydrochalcone (I) and,
wherein the total amount of component (a) is sufficient to enhance—preferably synergistically—the sweet taste of the sweet-tasting substance, in comparison to an otherwise equivalent composition without hesperetin dihydrochalcone (I) and/or salt(s) thereof, and
wherein the total amount of hesperetin dihydrochalcone (I) and/or salt(s) thereof is sufficient to reduce and/or mask the unpleasant taste of the bitter-, sour-, and/or astringent-tasting substance(s), and
wherein the total amount of hesperetin dihydrochalcone (I) and/or salt(s) thereof is sufficient to modulate the taste impressions of the components (h).

Further, particular preference is for an aroma composition comprising or consisting of the following components:
(a) a compound of formula (I) or a salt of the compound of formula (I) or a mixture comprising or consisting of a plurality of salts of the compound of formula (I), or a mixture comprising or consisting the compound of formula (I) and a salt or a plurality of salts of the compound of formula (I); and at least one or a plurality of the substances selected from the group consisting of substance(s) (c) and (d) or mixtures thereof, wherein
substance(s) (c) means one or more unpleasant-tasting substances, preferably bitter-, sour-, and/or astringent-tasting substances, in particular bitter-tasting substances
substance(s) (d) means one or more both sweet-tasting substances and unpleasant-tasting substances, in particular bitter-tasting substances; and
(e) homoeriodictyol or its sodium salts, and optionally at least one of the substances selected from the group consisting of eriodictyol, matairesinol, lariciresinol, naringenin, phloretin, 5-hydroxy-4-(4-hydroxy-3-methoxyphenyl)-7-methoxychroman-2-one, 5,7-dihydroxy-4-(4-hydroxyphenyl)chroman-2-one, 5,7-dihydroxy-4-(4-hydroxy-3-methoxyphenyl)chroman-2-one, or 2,4-dihydroxybenzoic acid vanillyl amide and optionally more substances to mask or reduce an unpleasant taste impression, in particular a bitter taste impression; and optionally comprises:
(b) one or more sweet-tasting substances; and/or
(f) one or more further substances for intensifying a sweet taste impression, particularly preferred selected from the group consisting of hesperetin, phloretin, rubusoside, fermented *rubus* extract according to EP 2,954,785-A1, naringenin, balansin A, Balansin B and phyllodulcin, and/or (g) one or more substances to mask or reduce a metallic, chalky, sour, or astringent taste impression, and/or (h) one or more substances having a taste impression selected from the group consisting of cooling, umami, fruity and spicy taste impression or mixtures thereof;

wherein components (b)-(h) do not comprise hesperetin dihydrochalcone (I) or a salt of hesperetin dihydrochalcone (I) and, wherein the total amount of component (a) is sufficient to enhance—preferably synergistically—the sweet taste of the sweet-tasting substance, in comparison to an otherwise equivalent composition without hesperetin dihydrochalcone (I) and/or salt(s) thereof, and wherein the total amount of hesperetin dihydrochalcone (I) and/or salt(s) thereof is sufficient to reduce and/or mask the unpleasant taste of the bitter-, sour-, and/or astringent-tasting substance(s), and wherein the total amount of hesperetin dihydrochalcone (I) and/or salt(s) thereof is sufficient to modulate the taste impressions of the components (h).

A or the sweet-tasting substance(s) (b) is or are preferably selected from the group consisting of vanillin, ethylvanillin, ethylvanillin isobutyrate (=3-ethoxy-4-isobutyryloxybenzaldehyde), Furaneol® (2,5-dimethyl-4-hydroxy-3(2H)-furanone) and derivatives thereof (e.g. homofuraneol, 2-ethyl-4-hydroxy-5-methyl-3(2H)-furanone), homofuronol (2-ethyl-5-methyl-4-hydroxy-3(2H)-fura none and 5-ethyl-2-methyl-4-hydroxy-3(2H)furanone), maltol and derivatives thereof (e.g. ethylmaltol), coumarin and derivatives thereof, gamma-lactones (e.g. gamma-undecalactone, gamma-nonalactone), delta-lactones (e.g. 4-methyl-delta-lactone, massoilactone, delta-decalactone, tuberolactone), methyl sorbate, divanillin, 4-hydroxy-2(or 5)-ethyl-5(or 2)-methyl-3 (2H)furanone, 2-hydroxy-3-methyl-2-cyclopentenones, 3-hydroxy-4,5-dimethyl-2(5H)-furanone, fruit esters and fruit lactones (e.g. n-butyl acetate, isoamyl acetate, ethyl propionate, ethyl butyrate, n-butyl butyrate, isoamyl butyrate, ethyl 3-methyl-butyrate, ethyl n-hexanoate, allyl n-hexanoate, n-butyl n-hexanoate, ethyl n-octanoate, ethyl-3-methyl-3-phenylglycidate, ethyl-2-trans-4-cis-decadienoate), 4-(p-hydroxyphenyl)-2-butanone, 1,1-dimethoxy-2,2, 5-trimethyl-4-hexane, 2,6-dimethyl-5-hepten-1-al, phenylacetaldehyde, sucrose, trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, erythritol, threitol, arabitol, ribitol, xylitol, sorbitol, mannitol, dulcitol and lactitol.

A or the unpleasant-, in particular bitter-, tasting substance(s) (c) is or are preferably selected from the group consisting of xanthine alkaloids, xanthines (caffeine, theobromine, theophylline), alkaloids (quinine, Chininhydrochloride, brucine, strychnine, nicotine), phenolic glycosides (e.g. salicin, arbutin), flavonoid glycosides (e.g. hesperidine, naringin), chalcones or chalcone glycosides, hydrolysable tannins (gallic or ellagic acid esters of carbohydrates, e.g. pentagalloylglucose), non-hydrolysable tannins (optionally galloylated catechols or epicatechols and oligomers thereof, e.g. proanthyocyanidines or procyani-dines, thearubigin), flavones (e.g. quercertin, taxifolin, myricetin), other polyphenols (gamma-oryzanol, coffeic acid or esters thereof), terpenoid bitter substances (e.g. limonoids such as limonine or nomilin from citrus fruits, lupolones and humulones from hops, iridoids, secoiridoids), absinthin from wormwood, amarogentin from gentian, metal salts (potassium chloride, sodium sulfate, magnesium salts, iron salts, aluminum salts, zinc salts), pharmaceutical active ingredients (e.g. fluoroquinolone antibiotics, beta-lactam antibiotics, ambroxol, propylthiouracil [PROP], aspirin (acetyl salicylic acid), salicin, paracetamol (acetaminophene), ibuprofen, naproxen, ambroxol, guafenesin, omeprazole, pantoprazole, dextromorphane, or quinine), vitamins (for example vitamin H, vitamins from the B group, such as vitamin B1, B2, B6, B12, niacin, pantothenic acid), denatonium benzoate or other denatonium salts, sucralose octaacetate, urea, unsaturated fatty acids, in particular unsaturated fatty acids in emulsions, amino acids (e.g. leucine, isoleucine, valine, tryptophan, proline, histidine, tyrosine, lysine or phenylalanine, in particular the respective L-enantiomers of leucine, isoleucine, valine, tryptophane, proline, histidine, tyrosine, lysine or phenylalanine), peptides (in particular peptides having an amino acid from the group L-leucine, L-isoleucine, L-valine, L-tryptophane, L-proline or L-phenylalanine at the N- or C-terminus).

A or the both sweet- and unpleasant-tasting substances (d) is or are preferably selected from the group consisting of steviolglycosides (in particular stevioside and rebaudioside A), rubusoside, dulcoside, mogroside, phyllodulcin, glycyrrhetin acid or extracts of *Stevia* ssp. (in particular *Stevia rebaudiana*), Luo Han Guo, *Rubus suavissimus, Hydrangea dulcis, Mycetia balansae, Glycyrrhyza glabra*, A or the substance(s) (e) to mask or reduce a bitter taste impression is or are preferably selected from the group consisting of sodium salts (e.g. sodium chloride, sodium lactate, sodium citrate, sodium acetate, sodium gluconoate), homoeriodictyol or its sodium salts, eriodictyol, matairesinol, lariciresinol, naringenin, phloretin, 5-hydroxy-4-(4-hydroxy-3-methoxyphenyl)-7-methoxychroman-2-one, 5,7-dihydroxy-4-(4-hydroxyphenyl)chroman-2-one, 5,7-dihydroxy-4-(4-hydroxy-3-methoxyphenyl)chroman-2-one, or 2,4-dihydroxybenzoic acid vanillyl amide, gamma-aminobutyric acid, pellitorine (in particular as described in EP 2008530 A1) and gingerdione, more preferably selected from the group consisting of sodium salts (e.g. sodium chloride, sodium lactate, sodium citrate, sodium acetate, sodium gluconoate).

A or the substance(s) (f) for intensifying a sweet taste impression, is or are preferably selected from the group consisting of hesperetin (in particular as disclosed in WO 2007/014879), hydroxyphenylalkane diones (in particular those described in WO 2007/003527), deoxybenzoins (in particular as described in WO 2006/106023 and German patent application DE10 2009 002 268.6), 4-hydroxychalcones (in particular as described in WO 2007/107596), propenylphenylglycosides (chavicol glycosides) (in particular as described in EP 1 955 601 A1), divanillins (in particular as described in WO 2004/078302), hydroxyflavans according to EP 2,253,226, dihydrochalcones according to EP 2,353,403 B1, naringin, phloretin, rubusoside, fermented *rubus* extract according to EP 2,954,785-A1, naringenin, balansin A, Balansin B and phyllodulcin.

The abovementioned documents are, with regard to the corresponding compounds disclosed therein, by way of reference part of this application.

An aroma composition according to the invention preferably comprises at least one or more further substance(s) (g) to mask or reduce a metallic, chalky, sour or astringent taste impression and/or a or a plurality of further substance(s) (h) to intensify a salty or umami taste impression. Preferred further substances to mask or reduce an unpleasant taste impression and/or to intensify a pleasant taste impression are described further on.

Particular preference is for an aroma composition (as described above), wherein the bitter-tasting substance (c) or the both sweet- and also bitter-tasting substance (d) is selected from the group consisting of steviolglycosides, in particular stevioside and rebaudiosides, preferably selected from the group consisting of rebaudioside A, rubusoside, dulcoside, mogroside, phyllodulcin, glycyrrhetin acid or extracts of *Stevia* ssp. (in particular *Stevia rebaudiana*), Luo Han Guo, *Rubus suavissimus, Mycetia balansae, Hydrangea dulcis* or *Glycyrrhyza glabra*.

In particular the present invention also concerns a use of an aroma composition according to the invention (as described above) for the intensification—preferably synergistic intensification—of the sweet taste of a sweet-tasting substance or mixture of substances (b) and to mask or reduce an unpleasant, preferably bitter-, sour-, and/or astringent-tasting substances, in particular bitter taste impression of an unpleasant-, in particular bitter-tasting substance or mixture of substances (c) and/or for intensifying—preferably synergistically—the sweet taste impressions and/or to reduce or mask the unpleasant, in particular bitter, taste impressions of the both sweet- and unpleasant-, in particular bitter-, tasting substance or mixture of substances (d) in a preparation intended as an oral pharmaceutical, as a cosmetic, for nutrition, as a food supplement, for oral care or pleasure, in particular in preparations according to the invention as described below. Particularly preferably an aroma composition according to the invention is used to improve the sensorial profile of sweet products for oral consumption.

Consequently the present invention also concerns a preparation comprising an aroma composition according to the invention as described above. The preparation according to the invention is preferably a preparation selected from the group consisting of preparations intended for nutrition, as a food supplement, for oral care or pleasure, cosmetic preparations, in particular for application in the region of the head, pharmaceutical preparations intended to be taken orally, flavouring mixtures for use in one of the abovementioned preparations, or semi-finished products for manufacturing one of the preparations mentioned above.

A person skilled in the art will understand that the individual ingredients of the aroma composition according to the invention must be present in the preparation according to the invention. According to the invention it is unimportant here if these ingredients are introduced into the preparation together or successively.

Particular preference is for a preparation intended for nutrition, as a food supplement, for oral care or pleasure, as a cosmetic or as a pharmaceutical to be taken orally (as described above) according to the invention, wherein the preparation based on the total weight of the preparation comprises 0.00001% by weight (0.1 ppm)-0.005% by weight (50 ppm), preferably 0.00005% by weight (0.5 ppm)-0.003 (30 ppm), and particularly preferred 0.0001% by weight (1 ppm)-0.001% by weight (10 ppm), hesperetin dihydrochalcone (I) and its salts.

Preparations according to the invention can also be in the form of semi-finished products in particular for the manufacture of a preparation intended for nutrition, as a food supplement, for oral care or pleasure, as a cosmetic or as a pharmaceutical to be taken orally or a flavouring mixture.

Particular preference is for a preparation according to the invention (as described above), wherein the preparation is a semi-finished product suitable for manufacturing a preparation intended for use in nutrition, as food supplement, as flavourings mixtures, for oral care or pleasure or as cosmetic preparation or as a pharmaceutical to be taken orally, in particular for use in nutrition and as flavourings mixtures.

Particular preference is for a semi-finished product or flavouring mixture (as described above), wherein the semi-finished product based on the total weight of the semi-finished product or flavouring mixture comprises 0.0001% by weight--95% by weight, especially 0.001% by weight--95% by weight, preferably 0.001-80% by weight, particularly preferably 0.01% by weight--50% by weight, of the hesperetin dihydrochalcone (I) and its salts.

The preparations for nutrition or pleasure for the purposes of this invention are for example bakery products (for example bread, dry biscuits, cakes, other pastry products), confectionery (for example chocolates, chocolate bar products, other bar products, fruit gums, hard and soft caramels, chewing gum), alcoholic or non-alcoholic beverages (for example coffee, tea, wine, beverages containing wine, beer, beverages containing beer, liqueurs, spirits, brandies, fruit-containing beverages, isotonic beverages, soft drinks, nectars, fruit and vegetable juices, fruit or vegetable juice preparations), instant beverages (for example instant cocoa beverages, instant tea beverages, instant coffee beverages), meat products (for example ham, fresh or cured sausage preparations, spiced or marinated fresh or cured meat products), eggs or egg products (dried egg, egg white, egg yolk), cereal products (for example breakfast cereals, muesli bars, precooked ready rice products), dairy products (for example milk beverages, milk ice cream, yoghurt, kefir, curd cheese, soft cheese, hard cheese, dried milk powder, whey, butter, buttermilk, partially or fully hydrolyzed milk protein-containing products), products made from soya protein or other soya bean fractions (for example soya milk and products made therefrom, soya lecithin-containing preparations, fermented products such as tofu or tempe or products made therefrom, soy sauce), fruit preparations (for example jams, fruit ice cream, fruit sauces, fruit fillings), vegetable preparations (for example ketchup, sauces, dried vegetables, deep-frozen vegetables, precooked vegetables, preserved vegetables, boiled down vegetables), snack articles (for example baked or fried potato chips or potato dough products, bread dough products, maize- or peanut-based extrudates), fat- or oil-based products or emulsions thereof (for example mayonnaise, remoulade, dressings, flavouring preparations), other ready-to-serve meals and soups (for example dried soups, instant soups, precooked soups), spices, seasoning mixtures and in particular powdered seasonings, which are for example used in snack food applications. The preparations for the purposes of the invention may also be used as semi-finished products for the production of further preparations serving for nutrition or for pleasure. The preparations for the purposes of the invention may also be nutritional supplements in the form of capsules, tablets (uncoated and coated tablets, for example having coatings resistant to gastric juices), sugar-coated tablets, granules, pellets, mixtures of solids, dispersions in liquid phases, as emulsions, as powders, as solutions, as pastes or as other swallowable or chewable preparations.

Pharmaceutical preparations for oral consumption for the purposes of the invention are preparations for example in the form of capsules, tablets (uncoated and coated tablets, for example having coatings resistant to gastric juices), sugar-coated tablets, granules, pellets, mixtures of solids, dispersions in liquid phases, as emulsions, as powders, as solutions, as pastes or as other swallowable or chewable preparations and are used as medicines only available by prescription, from pharmacies or other medicines or as food supplements.

The preparations serving for oral care for the purposes of this invention are in particular oral and/or dental care products such as toothpastes, tooth gels, tooth powders, mouthwashes, chewing gums and other oral care products. Particular preference is for preparations serving for oral care, containing an extract or components of an extract of Stevie ssp. hesperetin dihydrochalcone (I) is advantageously particularly well suited to masking or reducing in preparations serving for oral care containing steviolglycosides a bitter taste impression of the steviolglycosides, in particular of stevioside and/or rebaudioside A.

Cosmetic preparations, in particular cosmetic preparations for application in the region of the head, are in the context of this invention preferably cosmetic preparations that contain at least one unpleasant, preferably bitter-, sour-, and/or astringent-tasting substances, in particular a bitter-tasting substance (c) and even when applied correctly to the skin can come into contact with the oral cavity. Such preparations are for example cosmetic preparations for application in the region of the head, such as soaps, other cleansing or care agents for the facial region, face creams or lotions or ointments, sun protection agents, beard cleansing or care agents, shaving foams, soaps or gels, lipsticks or other cosmetics for the lips, or lip care agents.

Particularly preferably the present invention concerns a preparation according to the invention (as described above), which comprises as an ingredient one or more both sweet and bitter-tasting substance(s) (d), wherein the total quantity of hesperetin dihydrochalcone (I) or salts of the hesperetin dihydrochalcone (I) in the preparation is sufficient to both intensify—preferably synergistically—the sweet taste impression of the both sweet- and bitter-tasting substance(s) (d) and also to mask or reduce the bitter taste impression of the both sweet- and bitter-tasting substance(s) (d).

Particular preference is for a preparation according to the invention (as described above), in particular a preparation serving for nutrition, pleasure or oral care, wherein one, a plurality of or preferably all the both sweet- and bitter-tasting substance(s) (d) is or are selected from the group consisting of steviol glycosides, in particular from stevioside and rebaudioside A, preferably selected from the group consisting of rebaudioside A, rubusoside, dulcoside, mogroside, phyllodulcin, glycyrrhetin acid or extracts of *Stevia* ssp. (in particular *Stevia rebaudiana*), Luo Han Guo, *Rubus suavissimus, Hydrangea dulcis, Mycetia balansae* or *Glycyrrhyza glabra*.

Further preference is for a preparation according to the invention (as described above), in which the total quantity of bitter-tasting substances (c) and/or both sweet- and bitter-tasting substances (d) in the preparation is sufficient to be perceived as a bitter taste, and the total quantity of (i) hesperetin dihydrochalcone (I) and (ii) its salts (component (a)) in the preparation is sufficient, to mask the bitter taste of the bitter-tasting substance(s) (c) or of the both sweet- and bitter-tasting substance(s) (d), compared with a preparation which with an otherwise identical composition contains neither (i) hesperetin dihydrochalcone (I) nor (ii) its salts.

A preparation according to the invention preferably comprises also at least one further substance to mask or reduce a bitter, metallic, chalky, sour or astringent taste impression and/or to intensify a sweet, salty or umami taste impression.

Preference is also for a preparation according to the invention, in particular a preparation or semi-finished product (as described in each case above) serving for nutrition, oral care or pleasure or for cosmetics or intended for oral administration of pharmaceuticals, comprising an aroma composition according to the invention (as described above), wherein the aroma composition according to the invention as a proportion of the preparation according to the invention is 0.000001% by weight to 95% by weight, based on the total weight of the preparation.

The manufacture according to the invention of aroma compositions or preparations according to the invention comprises the steps (1) Providing the following components:
   (a) hesperetin dihydrochalcone (I) or a salt of the hesperetin dihydrochalcone (I) or a mixture comprising or consisting of a plurality of salts of the hesperetin dihydrochalcone (I) or a mixture comprising or consisting of hesperetin dihydrochalcone (I) and a salt or a plurality of salts of the hesperetin dihydrochalcone (I), and at least one or a plurality of the substances selected from the group consisting of substance(s) (c) and (d) or mixtures thereof, wherein
      substance(s) (c) means one or more unpleasant-tasting substances, preferably bitter-, sour-, and/or astringent-tasting substances, in particular bitter-tasting substances
      substance(s) (d) means one or more both sweet-tasting substances and unpleasant-tasting substances, in particular bitter-tasting substances; and/or
   (b) one or more sweet-tasting substances and/or
   (e) one or more substances to mask or reduce an unpleasant taste impression, in particular a bitter taste impression, and/or
   (f) one or more further substances for intensifying a sweet taste impression, and/or
   (g) one or more substances to mask or reduce a metallic, chalky, sour, or astringent taste impression, and/or
   (h) one or more substances having a taste impression selected from the group consisting of cooling, umami, fruity and spicy taste impression or mixtures thereof;
      wherein components (b)-(h) do not comprise hesperetin dihydrochalcone (I) or a salt of hesperetin dihydrochalcone (I) and, (2) mixing of components (a), (b), (c) and/or (d) with the further components.

In a preferred embodiment, the manufacture according to the invention of aroma compositions or preparations according to the invention comprises the steps (1) Providing the following components:
   (a) hesperetin dihydrochalcone (I) or a salt of the hesperetin dihydrochalcone (I) or a mixture comprising or consisting of a plurality of salts of the hesperetin dihydrochalcone (I) or a mixture comprising or consisting of hesperetin dihydrochalcone (I) and a salt or a plurality of salts of the hesperetin dihydrochalcone (I), and at least one or a plurality of the substances selected from the group consisting of substance(s) (c) and (d) or mixtures thereof, wherein
      substance(s) (c) means one or more unpleasant-tasting substances, preferably bitter-, sour-, and/or astringent-tasting substances, in particular bitter-tasting substances
      substance(s) (d) means one or more both sweet-tasting substances and unpleasant-tasting substances, in particular bitter-tasting substances; and
   (e) one or more substances to mask or reduce an unpleasant taste impression, in particular a bitter taste impression; and/or (b) one or more sweet-tasting substances, and/or
(f) one or more further substances for intensifying a sweet taste impression, particularly preferred selected from the group consisting of hesperetin, phloretin, rubusoside, fermented *rubus* extract according to EP 2,954,785-A1, naringenin, balansin A, Balansin B and phyllodulcin, and/or
(g) one or more substances to mask or reduce a metallic, chalky, sour, or astringent taste impression, and/or
(h) one or more substances having a taste impression selected from the group consisting of cooling, umami, fruity and spicy taste impression or mixtures thereof; wherein components (b)-(h) do not comprise hesperetin dihydrochalcone (I) or a salt of hesperetin dihydrochalcone (I) and,
(2) mixing of components (a), (b), (c), (e) and/or (d) with the further components.

In a particularly preferred embodiment, the manufacture according to the invention of aroma compositions or preparations according to the invention comprises the steps
(1) Providing the following components:
(a) hesperetin dihydrochalcone (I) or a salt of the hesperetin dihydrochalcone (I) or a mixture comprising or consisting of a plurality of salts of the hesperetin dihydrochalcone (I) or a mixture comprising or consisting of hesperetin dihydrochalcone (I) and a salt or a plurality of salts of the hesperetin dihydrochalcone (I), and at least one or a plurality of the substances selected from the group consisting of substance(s) (c) and (d) or mixtures thereof, wherein
substance(s) (c) means one or more unpleasant-tasting substances, preferably bitter-, sour-, and/or astringent-tasting substances, in particular bitter-tasting substances; and
substance(s) (d) means one or more both sweet-tasting substances and unpleasant-tasting substances, in particular bitter-tasting substances; and
(e) at least one of the substances selected from the group consisting of homoeriodictyol or its sodium salts, eriodictyol, matairesinol, lariciresinol, naringenin, phloretin, 5-hydroxy-4-(4-hydroxy-3-methoxyphenyl)-7-methoxychroman-2-one, 5,7-dihydroxy-4-(4-hydroxyphenyl)chroman-2-one, 5,7-dihydroxy-4-(4-hydroxy-3-methoxyphenyl)chroman-2-one and 2,4-dihydroxybenzoic acid vanillyl amide and optionally more substances to mask or reduce an unpleasant taste impression, in particular a bitter taste impression; and/or
(b) one or more sweet-tasting substances, and/or
(f) one or more further substances for intensifying a sweet taste impression, particularly preferred selected from the group consisting of hesperetin, phloretin, rubusoside, fermented *rubus* extract according to EP 2,954,785-A1, naringenin, balansin A, Balansin B and phyllodulcin, and/or
(g) one or more substances to mask or reduce a metallic, chalky, sour, or astringent taste impression, and/or
(h) one or more substances having a taste impression selected from the group consisting of cooling, umami, fruity and spicy taste impression or mixtures thereof; wherein components (b)-(h) do not comprise hesperetin dihydrochalcone (I) or a salt of hesperetin dihydrochalcone (I) and,
(2) mixing of components (a), (b), (c), (e) and/or (d) with the further components.

In other particularly preferred embodiment, the manufacture according to the invention of aroma compositions or preparations according to the invention comprises the steps
(1) Providing the following components:
(a) hesperetin dihydrochalcone (I) or a salt of the hesperetin dihydrochalcone (I) or a mixture comprising or consisting of a plurality of salts of the hesperetin dihydrochalcone (I) or a mixture comprising or consisting of hesperetin dihydrochalcone (I) and a salt or a plurality of salts of the hesperetin dihydrochalcone (I), and at least one or a plurality of the substances selected from the group consisting of substance(s) (c) and (d) or mixtures thereof, wherein
substance(s) (c) means one or more unpleasant-tasting substances, preferably bitter-, sour-, and/or astringent-tasting substances, in particular bitter-tasting substances
substance(s) (d) means one or more both sweet-tasting substances and unpleasant-tasting substances, in particular bitter-tasting substances, and
(e) homoeriodictyol or its sodium salts, and optionally at least one of the substances selected from the group consisting of eriodictyol, matairesinol, lariciresinol, naringenin, phloretin, 5-hydroxy-4-(4-hydroxy-3-methoxyphenyl)-7-methoxychroman-2-one, 5,7-dihydroxy-4-(4-hydroxyphenyl)chroman-2-one, 5,7-dihydroxy-4-(4-hydroxy-3-methoxyphenyl)chroman-2-one, or 2,4-dihydroxybenzoic acid vanillyl amide and optionally more substances to mask or reduce an unpleasant taste impression, in particular a bitter taste impression; and/or
(b) one or more sweet-tasting substances, and/or
(f) one or more further substances for intensifying a sweet taste impression, particularly preferred selected from the group consisting of hesperetin, phloretin, rubusoside, fermented *rubus* extract according to EP 2,954,785-A1, naringenin, balansin A, Balansin B and phyllodulcin, and/or
(g) one or more substances to mask or reduce a metallic, chalky, sour, or astringent taste impression, and/or
(h) one or more substances having a taste impression selected from the group consisting of cooling, umami, fruity and spicy taste impression or mixtures thereof; wherein components (b)-(h) do not comprise hesperetin dihydrochalcone (I) or a salt of hesperetin dihydrochalcone (I) and,
(2) mixing of components (a), (b), (c), (e) and/or (d) with the further components.

The preparations according to the invention comprising hesperetin dihydrochalcone (I) and/or its salts, are preferably manufactured in that hesperetin dihydrochalcone (I) and/or the salts(s) of the hesperetin dihydrochalcone (I) is or are incorporated with a solid or liquid excipient in the form of a solution or a mixture in a corresponding preparation, i.e. in particular serving for nutrition, as a food supplement, for oral care or pleasure or as a cosmetic, or a pharmaceutical (base) preparation intended for oral application. As a solution these preparations according to the invention can advantageously also be converted by spray drying into a solid preparation.

According to a further preferred embodiment, for manufacturing preparations according to the invention hesperetin dihydrochalcone (I) according to the invention and/or its salts and if necessary further ingredients of the preparation according to the invention can first (i.e. prior to incorporation in the preparation) be incorporated in emulsions, in liposomes, e.g. starting from phosphatidylcholine, in microspheres, in nanospheres or also in capsules, granules or extrudates in a matrix suitable for foodstuffs and semi-luxury foods, e.g. starch, starch derivatives, cellulose or cellulose derivatives (e.g. hydroxypropylcellulose), other polysaccharides (e.g. alginate), natural fats, natural waxes (e.g. beeswax, carnauba wax) or proteins, e.g. gelatin.

In a further preferred manufacturing method hesperetin dihydrochalcone (I) and/or its salts are first complexed with a plurality of suitable complexing agents, for example with cyclodextrins or cyclodextrin derivatives, preferably α- or β-cyclodextrin, and used in this complexed form.

Particular preference is for a preparation according to the invention in which the matrix is selected such that the hesperetin dihydrochalcone (I) and/or the salt(s) of the hesperetin dihydrochalcone (I) have a delayed release from the matrix so that a long-lasting effect is achieved.

As further ingredients for preparations according to the invention for nutrition or enjoyment basic substances, auxiliary substances and additives conventional for foodstuffs or semi-luxury foods can be contained in a preparation according to the invention (as described above) or used for the manufacture of such preparations, for example water, mixtures of fresh or processed, vegetable or animal base or raw substances (e.g. raw, roast, dried, fermented, smoked and/or boiled meat, bone, cartilage, fish, vegetables, fruits, herbs, nuts, vegetable or fruit juices or pastes or mixtures thereof), digestible or non-digestible carbohydrates (e.g. sucrose, maltose, fructose, glucose, dextrins, amylose, amylopectin, inulin, xylans, cellulose, tagatose), sugar alcohols (e.g. sorbitol, erythritol), natural or hardened fats (e.g. tallow, lard, palm oil, coconut fat, hardened vegetable fat), oils (e.g. sunflower oil, groundnut oil, maize oil, olive oil, fish oil, soybean oil, sesame oil), fatty acids or their salts (e.g. potassium stearate), proteinogenic or non-proteinogenic amino acids and related compounds (e.g. γ-minobutyric acid, taurine), peptides (e.g. glutathione), natural or processed proteins (e.g. gelatin), enzymes (e.g. peptidases), nucleic acids, nucleotides, other taste-correcting agents or taste modulators for unpleasant taste impressions or not unpleasant taste impressions, in particular taste-modulating substances (e.g. inositol phosphate, nucleotides such as guanosine monophosphate, adenosine monophosphate or other substances such as sodium glutamate or 2-phenoxypropionic acid), emulsifiers (e.g. lecithins, diacylglycerols, gum arabic), stabilizers (e.g. carrageenan, alginate), preservatives (e.g. benzoic acid, sorbic acid), antioxidants (e.g. tocopherol, ascorbic acid), chelators (e.g. citric acid), organic or inorganic acidifying agents (e.g. malic acid, acetic acid, citric acid, tartaric acid, phosphoric acid), (if necessary further) bitter substances (e.g. quinine, caffeine, limonine, amarogentin, humulones, lupolones, catechols, tannins), (if necessary further) sweeteners (e.g. saccharin, cyclamate, aspartame, neotame), mineral salts (e.g. sodium chloride, potassium chloride, magnesium chloride, sodium phosphates), substances that prevent enzymatic browning (e.g. sulfite, ascorbic acid), essential oils, plant extracts, natural or synthetic colourings or colouring pigments (e.g. carotinoids, flavonoids, anthocyanins, chlorophyll and derivatives thereof), spices, substances having trigeminal action or plant extracts containing such substances having trigeminal action, synthetic, natural or nature identical flavourings or fragrances and also odor-correcting agents.

Tooth care agents (as the basis for preparations according to the invention for oral care) generally comprise an abrasive system (abrasive or polishing agent), such as, for example, silicas, calcium carbonates, calcium phosphates, aluminum oxides and/or hydroxyl apatites, surface-active substances, such as, for example, sodium lauryl sulfate, sodium lauryl sarcosinate and/or cocamidopropylbetain, humectants, such as, for example, glycerol and/or sorbitol, thickeners, such as, for example, carboxymethylcellulose, polyethylene glycols, carrageenan and/or Laponite®, (if necessary further) sweeteners, such as, for example, saccharin, taste-correcting agents for unpleasant further taste impressions, or generally not unpleasant taste impressions, taste-modulating substances (e.g. inositol phosphate, nucleotides such as guanosine monophosphate, adenosine monophosphate or other substances such as sodium glutamate or 2-phenoxypropionic acid), cooling active ingredients, such as, for example, menthol, menthol derivatives (e.g. L-menthol, L-menthyl lactate, L-menthyl alkylcarbonates, menthone ketals, menthanecarboxylic acid amides), 2,2,2-trialkylacetic acid amides (e.g. 2,2-diisopropylpropionic acid methylamide), icilin derivatives, stabilizers and active ingredients, such as, for example, sodium fluoride, sodium monofluoro-phosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavourings and/or sodium bicarbonate or odor correcting agents.

Chewing gums (as a further example of preparations according to the invention serving for oral care) generally comprise a chewing gum base, that is to say a chewable mass which becomes plastic when chewed, sugars of various types, sugar substitutes, sweeteners, sugar alcohols, taste-correcting agents or taste modulators for further unpleasant or, generally not unpleasant taste impressions, taste-modulating substances (e.g. inositol phosphate, nucleotides such as guanosine monophosphate, adenosine monophosphate or other substances such as sodium glutamate or 2-phenoxypropionic acid), humectants, thickeners, emulsifiers, flavourings and stabilizers or odor-correcting agents.

As ingredients for oral pharmaceutical preparations according to the invention all basic substances, auxiliary substances and additives conventional for pharmaceutical preparations intended for oral use may be used. As active ingredients there can be used in particular also orally formulatable pharmaceutical active ingredients that have an unpleasant taste, in particular bitter-tasting substances, the bitter taste impression of which can be masked or reduced according to the invention. The active ingredients, basic substances, auxiliary substances and additives can be converted into the oral forms of administration in a manner known per se. This is generally effected using inert, non-toxic, pharmaceutically suitable auxiliary substances. These include inter alia carriers (e.g. microcrystalline cellulose), solvents (e.g. liquid polyethylene glycols), emulsifiers (e.g. sodium dodecylsulfate), dispersing agents (e.g. polyvinylpyrrolidone), synthetic and natural biopolymers (e.g. albumin), stabilizers (e.g. antioxidants such as ascorbic acid), colourings (e.g. inorganic pigments such as iron oxides) and odor-correcting agents as well as taste-correcting agents, in particular those that do not affect the bitter taste.

Preferably preparations according to the invention (as described above) can also contain an aroma composition (not according to the invention), in order to (further) complete and refine the taste and/or odor of the preparation. Suitable aroma compositions contain, for example, synthetic, natural or nature identical flavourings, fragrances and taste-imparting substances as well as suitable auxiliary substances and carriers. It is considered to be particularly advantageous that a bitter or metallic taste impression coming from aromas, fragrances or flavourings contained in the preparations according to the invention can be masked or reduced, so that the overall flavour or taste profile can be improved.

Preparations according to the invention in the form of semi-finished products can be used to mark or reduce an unpleasant taste impression of finished product preparations manufactured using the semi-finished preparation.

In a particularly preferred embodiment of this invention the hesperetin dihydrochalcone (I) to be used according to the invention or its salts is or are used in an aroma composition according to the invention or a preparation according to the invention containing an aroma composition according to the invention (as described above) in combination with at least one further substance for modifying, masking or reducing an unpleasant taste impression and/or for intensifying a pleasant taste impression, wherein the pleasant taste impression is preferably a sweet and/or umami taste. In this way a particularly effective masking effect can be achieved.

Further substances to mask or reduce an unpleasant taste impression and/or to intensify a pleasant taste impression or taste correcting agents are—without limiting this invention to these—preferably selected from the group consisting of nucleotides (for example adenosine-5'-monophosphate, cytidine-5'-monophosphate) or the pharmaceutically acceptable salts thereof, lactisoles, sodium salts (for example sodium chloride, sodium lactate, sodium citrate, sodium acetate, sodium gluconoate), hydroxyflavanones, for example eriodictyol, sterubin (eriodictyol-7-methylether), homoeriodictyol, and the sodium, potassium, calcium, magnesium or zinc salts thereof (in particular those as described in EP 1 258 200, which is part of this application by way of reference with respect to the corresponding compounds disclosed therein), hydroxybenzoic acid amides, for example 2,4-dihydroxybenzoic acid vanillylamide, 2,4-dihydroxybenzoic acid-N-(4-hydroxy-3-methoxybenzyl)amide, 2,4,6-trihydroxybenzoic acid-N-(4-hydroxy-3-methoxybenzyl)amide, 2-hydroxy-benzoic acid-N-4-(hydroxy-3-methoxybenzyl)amide, 4-hydroxybenzoic acid-N-(4-hydroxy-3-methoxybenzyl)amide, 2,4-dihydroxybenzoic acid-N-(4-hydroxy-3-methoxybenzyl)amidemono-sodium salt, 2,4-dihydroxybenzoic acid-N-2-(4-hydroxy-3-methoxyphenyl)ethylamide, 2,4-dihydroxybenzoic acid-N-(4-hydroxy-3-ethoxybenzyl)amide, 2,4-dihydroxybenzoic acid-N(3,4-dihydroxybenzyl)amide and 2-hydroxy-5-methoxy-N-[2-(4-hydroxy-3-methoxyphenyl)ethyl]amide; 4-hydroxybenzoic acid vanillylamide (in particular those as described in WO 2006/024587, which is part of this application by way of reference with respect to the corresponding compounds disclosed therein); hydroxydeoxybenzoins, for example 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone, 1-(2-hydroxy-4-methoxyphenyl)-2-(4-hydroxy-3-methoxyphenyl)ethanone) (in particular those as described in WO 2006/106023 which is part of this application by way of reference with respect to the corresponding compounds disclosed therein); hydroxyphenyl alkane diones, for example gingerdione-[2], gingerdione-[3], gingerdione-[4], dehydrogingerdione-[2], dehydrogingerdione-[3], dehydrogingerdione-[4]) (in particular those as described in WO 2007/003527 which is part of this application by way of reference with respect to the corresponding compounds disclosed therein); diacetyl trimers (in particular those as described in WO 2006/058893 which is part of this application by way of reference with respect to the corresponding compounds disclosed therein); gamma-aminobutyric acids (in particular those as described in WO 2005/096841 which is part of this application by way of reference with respect to the corresponding compounds disclosed therein); divanillins (in particular those as described in WO 2004/078302 which is part of this application by way of reference with respect to the corresponding compounds disclosed therein) and 4-hydroxydihydrochalcones (preferably as described in US 2008/0227867 A1, which is part of this application by way of reference with respect to the corresponding compounds disclosed therein), in this respect in particular phloretin and davidigenin, amino acids or mixtures of whey proteins with lecithins, hesperetin as disclosed in WO 2007/014879 which is part of this application by way of reference with respect to the corresponding compounds, 4-hydroxychalcones as disclosed in WO 2007/107596 which is part of this application by way of reference with respect to the corresponding compounds, or propylene phenyl glycosides (chavicolgylcosides) as described in EP 1 955 601 A1 which is part of this application by way of reference with respect to the corresponding compounds, pellitorin and derived flavouring compositions as described in U.S. Provisional Application 60/944,854 and in the patent applications based thereon, umami compounds as described in WO 2008/046895 and EP 1 989 944 A1 which are in each case part of this application by way of reference with respect to the corresponding compounds; matairesinol and neoflavanoide as described in WO 2012/146584 A1, US 2013 078192 A1 and US 2013 084252 A1, neoisoflavonoids as described in EP 2,570,035, EP 2,725,026 or EP 2,570,036, which are in each case part of this application by way of reference with respect to the corresponding compounds as well as umami compounds as described in U.S. Provisional Application 60/984,023 or U.S. Provisional Application 61/061,273 and in the patent applications based thereon, which are part of this application by way of reference with respect to the corresponding compounds disclosed therein.

Combinations with homoeriodictyol, eriodictyol and the sodium, potassium, calcium, magnesium or zinc salts of both compounds, matairesinol, neoflavanoids, divanillins, phloretin and/or hesperetin are particularly preferred.

A further aspect of the present invention concerns a method for masking, reducing or suppressing an unpleasant taste impression, preferably bitter, sour and/or astringent taste impression, of unpleasant-tasting substances or mixtures of substances, in particular bitter taste impression of bitter-tasting substances or mixtures of substances, and/or for modulating the taste impressions selected from the group consisting of cooling, sweet, umami, fruity and spicy notes of cooling-, sweet-, umami-, fruity- or spicy-tasting substances or mixtures of substances, and/or simultaneously for intensifying—preferably synergistically—the sweet-taste impression of sweet-tasting substances or mixtures of substances or both sweet- and bitter-tasting tasting substances or mixtures of substances with the following step
 mixing of the following components
(a) hesperetin dihydrochalcone (I) or a salt of the hesperetin dihydrochalcone (I) or a mixture comprising or consisting of a plurality of salts of the hesperetin dihydrochalcone (I) or a mixture comprising or consisting of hesperetin dihydrochalcone (I) and a salt or a plurality of salts of the hesperetin dihydrochalcone (I),
 and at least one or a plurality of the substances selected from the group consisting of substance(s) (c) and (d) or mixtures thereof, wherein substance(s) (c) means one or more unpleasant-tasting substances, preferably bitter-, sour-, and/or astringent-tasting substances, in particular bitter-tasting substances substance(s) (d) means one or more both sweet-tasting substances and unpleasant-tasting substances, in particular bitter-tasting substances; and/or (b) one or more sweet-tasting substances, and if necessary further components wherein components (b)-(h) do not comprise hesperetin dihydrochalcone (I) or a salt of hesperetin dihydrochalcone (I), and wherein the total quantity of component (a) in the mixture is sufficient to mask, reduce or suppress an unpleasant taste impression, preferably bitter, sour and/or astringent taste impression of unpleasant-tasting substances or mixtures of substances, in particular bitter taste impression of bitter tasting substances, and/or to modulate the taste impressions selected from the group consisting of cooling, umami, fruity and spicy notes of cooling-, umami-, fruity- or spicy-tasting substances or mixtures of substances. and simultaneously to intensify—preferably synergistically—the sweet-taste impression of sweet-tasting substances or mixtures of substances or both sweet- and bitter-tasting tasting substances or mixtures of substances.

In a preferred embodiment according to the present invention, the method for masking, reducing or suppressing an unpleasant taste impression, preferably bitter, sour and/or astringent taste impression, of unpleasant-tasting substances or mixtures of substances, in particular bitter taste impression of bitter-tasting substances or mixtures of substances, and/or for modulating the taste impressions selected from the group consisting of cooling, sweet, umami, fruity and spicy notes of cooling-, sweet-, umami-, fruity- or spicy-tasting substances or mixtures of substances, and/or simultaneously for intensifying—preferably synergistically—the sweet-taste impression of sweet-tasting substances or mixtures of substances or both sweet- and bitter-tasting tasting substances or mixtures of substances comprising the following step:
mixing of the following components
(a) hesperetin dihydrochalcone (I) or a salt of the hesperetin dihydrochalcone (I) or a mixture comprising or consisting of a plurality of salts of the hesperetin dihydrochalcone (I) or a mixture comprising or consisting of hesperetin dihydrochalcone (I) and a salt or a plurality of salts of the hesperetin dihydrochalcone (I),
and at least one or a plurality of the substances selected from the group consisting of substance(s) (c) and (d) or mixtures thereof, wherein
substance(s) (c) means one or more unpleasant-tasting substances, preferably bitter-, sour-, and/or astringent-tasting substances, in particular bitter-tasting substances
substance(s) (d) means one or more both sweet-tasting substances and unpleasant-tasting substances, in particular bitter-tasting substances; and
(e) one or more substances to mask or reduce an unpleasant taste impression, in particular a bitter taste impression; and/or
(b) one or more sweet-tasting substances, and if necessary further components
wherein components (b)-(h) do not comprise hesperetin dihydrochalcone (I) or a salt of hesperetin dihydrochalcone (I), and wherein the total quantity of component (a) in the mixture is sufficient to mask, reduce or suppress an unpleasant taste impression, preferably bitter, sour and/or astringent taste impression of unpleasant-tasting substances or mixtures of substances, in particular bitter taste impression of bitter tasting substances, and/or to modulate the taste impressions selected from the group consisting of cooling, umami, fruity and spicy notes of cooling-, umami-, fruity- or spicy-tasting substances or mixtures of substances, and simultaneously to intensify—preferably synergistically—the sweet-taste impression of sweet-tasting substances or mixtures of substances or both sweet- and bitter-tasting tasting substances or mixtures of substances.

In a particularly preferred embodiment according to the present invention, the method for masking, reducing or suppressing an unpleasant taste impression, preferably bitter, sour and/or astringent taste impression, of unpleasant-tasting substances or mixtures of substances, in particular bitter taste impression of bitter-tasting substances or mixtures of substances, and/or for modulating the taste impressions selected from the group consisting of cooling, sweet, umami, fruity and spicy notes of cooling-, sweet-, umami-, fruity- or spicy-tasting substances or mixtures of substances, and/or simultaneously for intensifying—preferably synergistically—the sweet-taste impression of sweet-tasting substances or mixtures of substances or both sweet- and bitter-tasting tasting substances or mixtures of substances comprising the following step
mixing of the following components
(a) hesperetin dihydrochalcone (I) or a salt of the hesperetin dihydrochalcone (I) or a mixture comprising or consisting of a plurality of salts of the hesperetin dihydrochalcone (I) or a mixture comprising or consisting of hesperetin dihydrochalcone (I) and a salt or a plurality of salts of the hesperetin dihydrochalcone (I), and at least one or a plurality of the substances selected from the group consisting of substance(s) (c) and (d) or mixtures thereof, wherein
substance(s) (c) means one or more unpleasant-tasting substances, preferably bitter-, sour-, and/or astringent-tasting substances, in particular bitter-tasting substances
substance(s) (d) means one or more both sweet-tasting substances and unpleasant-tasting substances, in particular bitter-tasting substances; and
(e) at least one of the substances selected from the group consisting of homoeriodictyol or its sodium salts, eriodictyol, matairesinol, lariciresinol, naringenin, phloretin, 5-hydroxy-4-(4-hydroxy-3-methoxyphenyl)-7-methoxychroman-2-one, 5,7-dihydroxy-4-(4-hydroxyphenyl)chroman-2-one, 5,7-dihydroxy-4-(4-hydroxy-3-methoxyphenyl)chroman-2-one and 2,4-dihydroxybenzoic acid vanillyl amide and optionally more substances to mask or reduce an unpleasant taste impression, in particular a bitter taste impression;
and/or
(b) one or more sweet-tasting substances. and if necessary further components
wherein components (b)-(h) do not comprise hesperetin dihydrochalcone (I) or a salt of hesperetin dihydrochalcone (I), and
wherein the total quantity of component (a) in the mixture is sufficient to mask, reduce or suppress an unpleasant taste impression, preferably bitter, sour and/or astringent taste impression of unpleasant-tasting substances or mixtures of substances, in particular bitter taste impression of bitter tasting substances, and/or
to modulate the taste impressions selected from the group consisting of cooling, umami, fruity and spicy notes of cooling-, umami-, fruity- or spicy-tasting substances or mixtures of substances, and simultaneously
to intensify—preferably synergistically—the sweet-taste impression of sweet-tasting substances or mixtures of substances or both sweet- and bitter-tasting tasting substances or mixtures of substances.

In other particularly preferred embodiment according to the present invention, the method for masking, reducing or suppressing an unpleasant taste impression, preferably bitter, sour and/or astringent taste impression, of unpleasant-tasting substances or mixtures of substances, in particular bitter taste impression of bitter-tasting substances or mixtures of substances, and/or
for modulating the taste impressions selected from the group consisting of cooling, sweet, umami, fruity and spicy notes of cooling-, sweet-, umami-, fruity- or spicy-tasting substances or mixtures of substances, and/or simultaneously
for intensifying—preferably synergistically—the sweet-taste impression of sweet-tasting substances or mixtures of substances or both sweet- and bitter-tasting tasting substances or mixtures of substances, comprising the following step
mixing of the following components
(a) hesperetin dihydrochalcone (I) or a salt of the hesperetin dihydrochalcone (I) or a mixture comprising or consisting of a plurality of salts of the hesperetin dihydrochalcone (I) or a mixture comprising or consisting of hesperetin dihydrochalcone (I) and a salt or a plurality of salts of the hesperetin dihydrochalcone (I), and at least one or a plurality of the substances selected from the group consisting of substance(s) (c) and (d) or mixtures thereof, wherein
substance(s) (c) means one or more unpleasant-tasting substances, preferably bitter-, sour-, and/or astringent-tasting substances, in particular bitter-tasting substances
substance(s) (d) means one or more both sweet-tasting substances and unpleasant-tasting substances, in particular bitter-tasting substances; and
(e) homoeriodictyol or its sodium salts, and optionally at least one of the substances selected from the group consisting of eriodictyol, matairesinol, lariciresinol, naringenin, phloretin, 5-hydroxy-4-(4-hydroxy-3-methoxyphenyl)-7-methoxychroman-2-one, 5,7-dihydroxy-4-(4-hydroxyphenyl)chroman-2-one, 5,7-dihydroxy-4-(4-hydroxy-3-methoxyphenyl)chroman-2-one, or 2,4-dihydroxybenzoic acid vanillyl amide and optionally more substances to mask or reduce an unpleasant taste impression, in particular a bitter taste impression; and/or
(b) one or more sweet-tasting substances and if necessary further components,
wherein components (b)-(h) do not comprise hesperetin dihydrochalcone (I) or a salt of hesperetin dihydrochalcone (I), and
wherein the total quantity of component (a) in the mixture is sufficient to mask, reduce or suppress an unpleasant taste impression, preferably bitter, sour and/or astringent taste impression of unpleasant-tasting substances or mixtures of substances, in particular bitter taste impression of bitter tasting substances, and/or
to modulate the taste impressions selected from the group consisting of cooling, umami, fruity and spicy notes of cooling-, umami-, fruity- or spicy-tasting substances or mixtures of substances, and simultaneously
to intensify—preferably synergistically—the sweet-taste impression of sweet-tasting substances or mixtures of substances or both sweet- and bitter-tasting tasting substances or mixtures of substances.

Preference is for a variant of the method according to the invention, wherein the total quantity of components (a) in the mixture is sufficient to
to mask, reduce or suppress an unpleasant taste impression, preferably bitter, sour and/or astringent taste impression of unpleasant-tasting substances or mixtures of substances, in particular bitter taste impression of bitter tasting substances, and/or
to enhance—preferably synergistically—the sweet taste of the sweet-tasting substance, and and/or to intensify—preferably synergistically—the sweet taste impression of a both sweet- and unpleasant-, in particular bitter tasting substances or mixture of substances and to reduce or modify the unpleasant, in particular bitter, taste impression of the both sweet—unpleasant, in particular bitter-tasting substances or mixtures of substances.

A further preference is for a variant of the method according to the invention, wherein the total quantity of components (a) in the mixture is sufficient to
to mask, reduce or suppress an unpleasant taste impression, preferably bitter, sour and/or astringent taste impression of unpleasant-tasting substances or mixtures of substances, in particular bitter taste impression of bitter tasting substances, and
to modulate the taste impressions selected from the group consisting of cooling, umami, fruity and spicy notes of cooling-, umami-, fruity- or spicy-tasting substances or mixtures of substances, and
to enhance—preferably synergistically—the sweet taste of the sweet-tasting substance, and/or
to intensify—preferably synergistically—the sweet taste impression of a both sweet- and unpleasant-, in particular bitter tasting substances or mixture of substances and to reduce or modify the unpleasant, in particular bitter, taste impression of the both sweet—unpleasant, in particular bitter-tasting substances or mixtures of substances.

A further preference is for a variant of the method according to the invention, wherein the total quantity of components (a) in the mixture is sufficient to
to mask, reduce or suppress an unpleasant taste impression, preferably bitter, sour and/or astringent taste impression of unpleasant-tasting substances or mixtures of substances, in particular bitter taste impression of bitter tasting substances, and
to modulate the taste impressions selected from the group consisting of cooling, umami, fruity and spicy notes of cooling-, umami-, fruity- or spicy-tasting substances or mixtures of substances, and
to enhance—preferably synergistically—the sweet taste of the sweet-tasting substance, and
to intensify—preferably synergistically—the sweet taste impression of a both sweet- and unpleasant-, in particular bitter tasting substances or mixture of substances and to reduce or modify the unpleasant, in particular bitter, taste impression of the both sweet—unpleasant, in particular bitter-tasting substances or mixtures of substances.

This last variant of the method is particularly preferred.

For further preferred embodiments of a method according to the invention, especially concerning hesperetin dihydrochalcone (I) and its salts and the preferred choice of substances (b), (c), (d) or (e) that stated above applies accordingly.

The invention will be further described in the following on the basis of examples. The examples serve to illustrate the invention, without thereby restricting the scope of protection of the claims. All numerical information relates to weight, unless stated otherwise.

Example 1

Synthesis of 3-(3-Hydroxy-4-methoxy-phenyl)-1-(2,4,6-trihydroxyphenyl)propan-1-one (hesperetin dihydrochalcone (I))

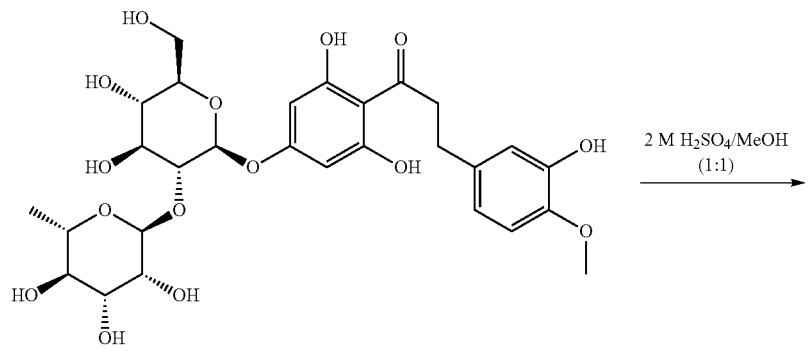

Neohesperidin dihydrochalcone

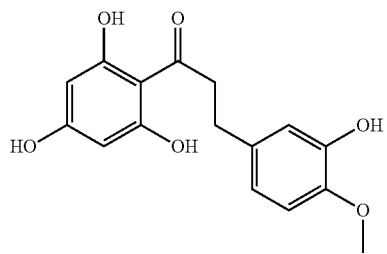

1

Neohesperidin dihydrochalcone in a mixture 2 M $H_2SO_4$/MeOH (1:1) was heated for 6 hours under reflux. After cooling to room temperature the reaction mixture was neutralized by addition of 2M NaOH and filtrated. The obtained solid product was washed with water (3×) and dried at 40° C. under vacuum to afford hesperetin dihydrochalcone (I) as a white solid product (Yield: 77%).

$^1$H-NMR (400 MHz, DMSO-$d_6$): δ=12.25 (s, 2H), 10.36 (s, 1H), 8.79 (s, 1H), 6.80 (d, J=8.2 Hz, 1H), 6.66 (d, J=2.1 Hz, 1H), 6.59 (dd, J=8.2, 2.2 Hz, 1H), 5.81 (s, 2H), 3.72 (s, 3H), 3.22 (dd, J=8.5, 6.9 Hz, 2H), 2.74 (dd, J=8.5, 6.9 Hz, 2H).

$^{13}$C NMR (101 MHz, DMSO-$d_6$): δ=203.97, 164.51, 164.12 (2C), 146.19, 145.70, 134.13, 118.59, 115.61, 112.24, 103.60, 94.54 (2C), 55.59, 45.11, 29.42.

Example 2

Bitter-Reduction of a Bitter Substance Solution

In order to quantify the decrease (i.e. the masking or reduction) in bitter impression in a specimen, the bitterness of a solution containing different bitter tasting substances in specific concentrations was compared by a group of experts (n=18) in each case with a specimen having an equivalent composition and additionally a specific concentration of hesperetin dihydrochalcone (I) (rating: 1 [not bitter] to 100 [extremely bitter]).

For the assessment, i.e. the calculation of the reduction (in %) of the bitter impression in each case the average values of the assessments of the group of experts for the respective bitter substance solution and the bitter substance solution also containing 10 ppm hesperetin dihydrochalcone (I) were used (*sign.lev. α=0.05). For comparison issues, the calculation of the reduction (in %) of the bitter impression for the respective bitter substance solution containing deoxy hesperetin dihydrochalcone is also included.

TABLE 1

Performance study

| Bitter Substance | Bitter impression of bitter substance (average values) | Bitter impression of bitter substance + compound (I) (average values) | Reduction in bitter impression by adding 10 ppm of compound (I) | Reduction in bitter impression by adding 50 ppm of deoxy hesperetin dihydrochalcone |
|---|---|---|---|---|
| 500 ppm Coffeine | 43.44 | 37.46 | −13.8% | −11.3% |
| 100 ppm Naringin | 59.29 | 46.54 | −21.5%* | −6.6% |
| 300 ppm Theobromine | 51.35 | 45.01 | −12.4% | n.d. |
| 250 ppm Salicin | 62.35 | 51.40 | −17.6%* | −15.2% |
| 5 ppm Chininhydrochloride | 38.72 | 29.05 | −25.0% | +10.7% |

It was surprisingly found that it was necessary an amount of deoxy hesperetin dihydrochalcone in factor 5 higher that the respective amount of hesperetin dihydrochalcone (I) in order to obtain a similar effect in the reduction of the bitter impression.

It was also shown, that in case of Naringin a notable increase in the reduction of the bitter impression was achieved by hesperetin dihydrochalcone (I) compared to deoxy hesperetin dihydrochalcone. Further, whereas 50 ppm of deoxy hesperetin dihydrochalcone shows no reduction of the bitter impression of Chininhydrochloride, a remarkable reduction of the bitter impression of Chininhydrochloride by only 10 ppm of hesperetin dihydrochalcone (I) was achieved.

Example 3

Intensification of the Sweet Impression of a Sugar Solution

In order to quantify the intensification of the sweet impression, in each case the sweetness of a 5% sucrose solution was compared by a group of experts with a specimen containing 5% sucrose and 1 ppm, 5 ppm, 7 ppm or 10 ppm of the hesperetin dihydrochalcone (I) to be used according to the invention (rating: 1 [not sweet] to 10 [extremely sweet]). For comparison issues, the intensification of the sweet impression containing with a specimen containing 5% sucrose and 10 ppm or 25 ppm deoxy hesperetin dihydrochalcone is also included.

For the assessment, i.e. calculation of the intensification (in %) of the sweet impression in each case the average values of the assessments of the group of experts for the sucrose solution and the specimen for comparison containing sucrose and hesperetin dihydrochalcone (I) or deoxy hesperetin dihydrochalcone were used.

TABLE 2

Performance study

Sweet impression (1-10)

| Test-(comparative)-substance | Sucrose (Sweetener) | Sucrose solution | Specimen (Sucrose + Test substance) | Intensification of the sweet impression |
|---|---|---|---|---|
| 1 ppm hesperetin dihydrochalcone (I) | 5% | 5.3 | 6.1 | 14.1% ($\alpha = 0.05$) |
| 5 ppm hesperetin dihydrochalcone (I) | 5% | 5.3 | 7.1 | 32.6% ($\alpha = 0.05$) |
| 7 ppm hesperetin dihydrochalcone (I) | 5% | 5.4 | 7.3 | 35.7% ($\alpha = 0.05$) |
| 10 ppm hesperetin dihydrochalcone (I) | 5% | 5.6 | 7.8 | 38.6% ($\alpha = 0.05$) |
| 10 ppm deoxy hesperetin dihydrochalcone | 5% | 5.3 | 6.4 | 21.2% ($\alpha = 0.05$) |
| 25 ppm deoxy hesperetin dihydrochalcone | 5% | 4.9 | 6.9 | 42% ($\alpha = 0.003$) |

It was surprisingly found that a remarkable intensification of the sweet impression is achieved by using hesperetin dihydrochalcone (I) in an amount of 10 ppm compared to the intensification of the sweet impression obtained using the same amount (10 ppm) of deoxy hesperetin dihydrochalcone.

Still further, it was surprisingly found that the increase of the intensification of the sweet impression using hesperetin dihydrochalcone (I) in an amount of 5 ppm was clearly higher as the intensification of the sweet impression using deoxy hesperetin dihydrochalconein an amount of 10 ppm.

Example 4

Intrinsic Sweetness of Hesperetin Dihydrochalcone (I)

A group of 30 experts were asked in a two-alternative forced choice (2AFC) test to select the solution with the stronger sweet impression from a couple of solutions. The evaluated solutions-couples are selected from a group of solutions consisting of a solution of hesperetin dihydrochalcone (I) in water (20 ppm, 15 ppm, 12.5 ppm, and 10 ppm) and a 1.5 wt % aqueous sucrose solution.

A solution of 10 ppm hesperetin dihydrochalcone (I) was described as remarkably weaker in regard to the sweet impression compared to the 1.5 wt % aqueous sucrose solution ($\alpha=0.05$).

Example 5

Modification of the Sweet Profile

The taste profile of a 7 wt % aqueous sucrose solution was compared with by a group of experts (n=12) in each case with a specimen having an equivalent composition and additionally a 1.5% sucrose (B), 5 ppm, 7 ppm or 20 ppm hesperetin dihydrochalcone (I).

TABLE 3

Performance study

| | Test solution | Beginning of sweet impression (<2 sec) | Overall sweet impression | Sugar full flavour and taste |
|---|---|---|---|---|
| A | 7% Sucrose-solution | 3.55 | 3.95 | 3.30 |
| B | 7% Sucrose-solution + 1.5% Sucrose (=8.5% sucrose solution) | 5.74 | 6.36 | 5.17 |
| C | 7% Sucrose-solution + 5 ppm hesperetin dihydrochalcone (I) | 4.63 | 5.24 | 4.26 |
| D | 7% Sucrose-solution + 7 ppm hesperetin dihydrochalcone (I) | 4.78 | 5.93 | 4.42 |
| E | 7% Sucrose-solution + 20 ppm hesperetin dihydrochalcone (I) | 4.49 | 4.90 | 4.11 |

As summarized in the table of above, hesperetin dihydrochalcone (I) does not only increases the determinated overall sweet impression, but in particular has an positive influence in the beginning of sweet impression (sweet impact) and the perceived sugar full flavour and taste. Therefore, a surprising improvement in the sensory properties was achieved.

Example 6

Improvement of the Taste Profile of Chicken Flavour

A group of experts (n=3) evaluated the influence on the taste profile of a chicken flavour with the typical descriptors of chicken meat note, boiled note, bony, light sour by the addition of 2 ppm hesperetin dihydrochalcone (I). A remarkably enhance of the mouth fullness without a negative influence on the above mentioned taste profile was achieved.

Example 7

Modulation of the Cooling-Profile of WS-3

A group of experts (n=5) evaluated the influence on the cooling profile of an aqueous solution containing 5 wt % sucrose and 4 ppm WS-3. An otherwise equivalent composition having additionally 1 ppm hesperetin dihydrochalcone (I) showed a faster perception of cooling impression and also a slightly improvement of the cooling effect.

Application Examples

Application Example 1

Spray-Dried Preparation as a Semi-Finished Product for Flavouring of Finished Products

| | Use in % by weight Preparation | | | | |
|---|---|---|---|---|---|
| Ingredient | A | B | C | D | E |
| Drinking water | 60.8 | 60.8 | 60.8 | 60.8 | 60.8 |
| Maltodextrin from wheat | 31.5 | 29.7 | 28.8 | 27.0 | 27.9 |
| Gum Arabic | 6.1 | 6.1 | 6.1 | 6.1 | 6.1 |
| Hesperetin dihydrochalcone (I) | 1.6 | 1.2 | 1.0 | 0.6 | 0.8 |
| Hesperetin | — | 2.2 | — | — | 1.1 |
| Homoeriodictyol-sodium salt | — | — | — | 5.5 | 3.3 |
| Phloretin | — | — | 3.3 | — | — |

The drinking water is placed in a container and maltodextrin and gum arabic is dissolved in it. Then the flavouring is emulsified in the carrier solution with a Turrax. The temperature of the spray solution should not exceed 30° C. The mixture is then spray-dried (inlet nominal temperature: 185-195° C., outlet nominal temperature: 70-75° C.).

Application Example 2

Combination with Sweeteners 90 g sucrose and 10 g tagatose are added to 0.5 g of a spray-dried semi-finished product from application example 1 (according to preparation A) and mixed. The product can for example be used as a sweetener with a bitter masking effect for coffee or tea.

Application Example 3

Chewing Gum

| Part | Ingredient | % b.w. |
|---|---|---|
| A | Chewing gum base from „Jagum T" company | 30.0 |
| B | Sorbitol, powdered | 39.0 |
| | Isomalt ® (Palatinit GmbH) | 9.5 |
| | Xylitol | 2.0 |
| | Mannitol | 3.0 |
| | Rebaudioside A 98% | 0.2 |
| | Emulgum ® (Colloides Naturels, Inc.) | 0.3 |
| C | Sorbitol, 70% | 14.0 |
| | Glycerin | 1.0 |
| D | Flavouring, containing 0.1 Gew.-% hesperetin dihydrochalcone (I) based on the total weight of the flavouring | 1.0 |

Parts A to D are mixed and kneaded intensively. The raw mass can be processed by way of example in the form of thin strips into ready-to-consume chewing gum.

Application Example 4

Toothpaste

| Part | Ingredient | % b.w. |
|------|-----------|--------|
| A | Demineralized water | 22.00 |
|   | Sorbitol (70%) | 46.00 |
|   | Solbrol ® M, sodium salt (Bayer AG, p-hydroxybenzoic acid alkyl ester) | 0.15 |
|   | Trisodium phosphate | 0.10 |
|   | Rebaudioside A, 98% | 0.10 |
|   | Sodium monofluorophosphate | 1.12 |
|   | Polyethylene glycol 1500 | 5.00 |
| B | Sident 9 (abrasive silicon dioxide) | 10.00 |
|   | Sident 22 S (thickening silicon dioxide) | 8.00 |
|   | Sodium carboxymethylcellulose | 0.90 |
|   | Titanium dioxide | 0.50 |
| C | Demineralized water | 4.63 |
|   | Sodium lauryl sulfate | 1.50 |
| D | Flavouring, containing 0.1 Gew.-% hesperetin dihydrochalcone (I) based on the total weight of the flavouring | 1.00 |

The ingredients of parts A and B are in each case pre-mixed separately and stirred well under a vacuum at 25-30° C. for 30 minutes. Part C is pre-mixed and added to A and B; D is added and the mixture stirred well under a vacuum at 25-30° C. for 30 minutes. After pressure relief the toothpaste is finished and can be filled.

Application Example 5

Sugar-Free Hard Boiled Candy

| | Content (%) | | | |
|---|---|---|---|---|
| Ingredient | A | B | C | D |
| Palatinite, Type M | 75.00 | 74.00 | 75.50 | 75.00 |
| Citric acid | — | 1.00 | 0.50 | — |
| Colouring, yellow | — | 0.01 | — | — |
| Colouring, red | — | — | 0.01 | — |
| Colouring, blue | 0.01 | — | — | 0.01 |
| Peppermint flavouring | 0.1 | — | — | 0.1 |
| Lemon flavouring | — | 0.1 | — | — |
| Red fruit flavouring | — | — | 0.1 | — |
| Rebaudioside A 98% | — | 0.040 | — | 0.040 |
| hesperetin dihydrochalcone (I) | 0.001 | 0.0005 | 0.001 | 0.0005 |
| Hesperetin | — | 0.001 | — | 0.001 |
| Phloretin | — | 0.002 | — | — |
| Water | ad 100 | | | |

Palatinite was mixed with water and the mixture melted at 165° C. and then cooled to 115° C. The other ingredients were added and after mixing cast into moulds, following hardening removed from the moulds and then individually packaged.

Application Example 6

Sugar-Reduced Tomato Ketchup

A: Comparative preparation with sugar

B: Comparative preparation with reduced sugar content (compared to A)

C-H: Preparations according to the invention with reduced sugar content (compared to A) and hesperetin dihydrochalcone (1)

| | Preparation (amounts in % by weight) | | | | | | | |
|---|---|---|---|---|---|---|---|---|
| Ingredient | A | B | C | D | E | F | G | H |
| Common salt | 2.0 | 2.0 | 2.0 | 2.0 | 2.0 | 2.0 | 2.0 | 2.0 |
| Starch, Farinex WM 55 | 1.0 | 1.0 | 1.0 | 1.0. | 1.0 | 1.0 | 1.0 | 1.0 |
| Sucrose | 12.0 | 9.6 | 9.2 | 8.4 | 9.6 | 9.6 | 8.4 | 8.4 |
| Tomato concentrate × 2 | 40.0 | 40.0 | 40.0 | 40.0 | 30.0 | 30.0 | 30.0 | 30.0 |
| Glucose syrup 80 Brix | 18.0 | 18.0 | 18.0 | 18.0 | 18.0 | 18.0 | 18.0 | 18.0 |
| Spirit vinegar 10% | 7.0 | 7.0 | 7.0 | 7.0 | 3.0 | 3.0 | 3.0 | 3.0 |
| Hesperetin dihydrochalcone (I) 0.5% in 1,2-Propylene glycol | | | 0.2 | 0.1 | 0.1 | 0.2 | 0.1 | 0.1 |
| Hesperetin 2.5% in 1,2-Propylene glycol | | | | | | 0.1 | | 0.2 |
| Phloretin 2.5% in 1,2-Propylene glycol | | | | | 0.2 | 0.2 | | 0.2 |
| Water | ad 100 | | | | | | | |

The ingredients are mixed in the stated sequence and the finished ketchup is homogenized using an agitator, poured into bottles and sterilized.

Application Example 7

Reduced-Sugar Fruit Gums

| Ingredient | A (% by weight), Comparative preparation | B ((% by weight), preparation according to the present invention |
|---|---|---|
| Water | 23.70 | 25.80 |
| Saccharose | 34.50 | 8.20 |
| Glucose syrup, DE 40 | 31.89 | 30.09 |
| Iso Syrup C* Tru Sweet 01750 (Cerestar) | 1.50 | 2.10 |
| Gelatin 240 Bloom | 8.20 | 9.40 |
| Polydextrose (Litesse ® Ultra, Danisco Cultor GmbH) | — | 24.40 |
| Yellow and red colourings | 0.01 | 0.01 |

-continued

| Ingredient | A (% by weight), Comparative preparation | B ((% by weight), preparation according to the present invention |
|---|---|---|
| Citric acid | 0.20 | — |
| Cherry flavouring, containing 1% by weight of hesperetin dihydrochalcone (I) based on the flavouring | — | 0.10 |

Note: Polydextrose is itself a non-sweet-tasting polysaccharide with a low calorific value.

Application Example 8

Gelatine Capsules for Direct Consumption

| Ingredient | A (% by weight) | B (% by weight) | C (% by weight) |
|---|---|---|---|
| Gelatine shell: | | | |
| Glycerin | 2.014 | 2.014 | 2.014 |
| Gelatine 240 Bloom | 7.91 | 7.91 | 7.91 |
| Sucralose | 0.065 | 0.065 | 0.065 |
| Allura red | 0.006 | 0.006 | 0.006 |
| Brillant blue | 0.005 | 0.005 | 0.005 |
| Core composition: | | | |
| Vegetable oil-triglyceride (coconut oil fraction) | 79.55 | 68.70 | 77.60 |
| Orange flavouring containing 0.005% by weight hesperetin dihydrochalcone (I) based on the total weight of the flavouring | 10.00 | 20.00 | 10.00 |
| Rebaudioside A 98% | 0.05 | 0.05 | — |
| 2-hydroxypropylmenthylcarbonate | 0.33 | 0.20 | — |
| 2-hydroxyethylmenthylcarbonate | — | 0.20 | 1.00 |
| (1R,3R,4S) menthyl-3-carboxylic-acid-N-ethylamide (WS-3) | — | 0.55 | 0.50 |
| (−)-Menthone glycerin acetal (Frescolat MGA) | — | 0.30 | 0.80 |
| Vanillin | 0.07 | — | 0.10 |

The gelatine capsules suitable for direct consumption were prepared according to WO 2004/050069 and had a diameter of 5 mm and the weight ratio of core material to shell material was 90:10. The capsules opened in the mouth in less than 10 seconds and dissolved completely in less than 50 seconds.

Application Example 9

Carbonated Drink (Flavour Direction: Cola)

A: drink containing sugar (comparative) drink
B: low-calorie drink
C: low-calorie drink
D: low-calorie drink
E: low-calorie drink

| Ingredient | A (% by weight) | B (% by weight) | C (% by weight) | D (% by weight) | E (% by weight) |
|---|---|---|---|---|---|
| Phosphoric acid 85% | 0.635 | 0.635 | 0.635 | 0.635 | 0.635 |
| Citric acid, anhydrous | 0.064 | 0.064 | 0.064 | 0.064 | 0.064 |
| Caffeine | 0.064 | 0.064 | 0.064 | 0.064 | 0.064 |
| Sucrose | 63.60 | — | — | — | 12.9 |
| Sucralose | — | 0.126 | — | — | — |
| Erythritol | — | — | 6.000 | — | — |
| Aspartame | — | — | 0.350 | — | 0.07 |
| Stevioside | — | — | — | 0.300 | — |
| Acesulfame K | — | — | — | — | 0.07 |
| Sugar colouring | 0.800 | 0.800 | 0.800 | 0.800 | 0.800 |
| Cola type drink emulsion | 1.445 | 1.445 | 1.445 | 1.445 | 1.445 |
| Sodium benzoate | 0.106 | 0.106 | 0.106 | 0.106 | 0.106 |
| Hesperetin dihydrochalcone (I) 0.5% in 1,2-propylene glycol | — | 1.0 | 1.0 | 1.0 | 1.0 |
| Water | | | ad 100 | | |

The solid components or ingredients are individually mixed with water, combined and made up to 100 g with water. The concentrate obtained is then allowed to age over night at ambient temperature. Finally, 1 part concentrate is mixed with 5 parts carbonated water, filled into bottles and sealed.

The invention claimed is:

1. A method for masking, reducing, and/or suppressing an unpleasant taste impression of an unpleasant tasting substance and/or for modulating a cooling, an umami, a fruity, and/or a spicy taste impression of a cooling, an umami, a fruity, and/or a spicy tasting substance, the method comprising mixing:
   (i) hesperetin dihydrochalcone (I) (3-(3-Hydroxy-4-methoxy-phenyl)-1-(2,4,6-trihydroxyphenyl)propan-1-one),

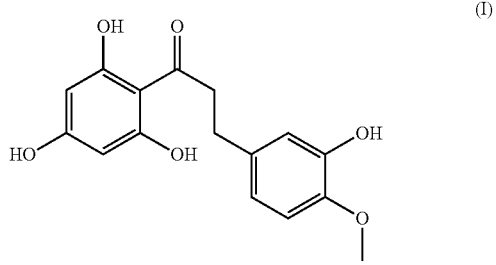 [SMILES: COc1ccc(CCC(=O)c2c(O)cc(O)cc2O)cc1O]

a salt of the hesperetin dihydrochalcone (I), a mixture of a plurality of salts of the hesperetin dihydrochalcone (I), or a mixture of the hesperetin dihydrochalcone (I) and a salt or a plurality of salts of the hesperetin dihydrochalcone (I), and
   (ii) an unpleasant, a cooling, an umami, a fruity and/or a spicy tasting substance,
   wherein the method intensifies a sweet-taste impression of a sweet-tasting substance, a mixture of sweet-tasting substances, both a sweet- and bitter-tasting substance, or a mixture of both sweet- and bitter-tasting substances,
   wherein
   the unpleasant-tasting substance is selected from the group consisting of xanthine alkaloids, xanthines, alkaloids, phenolic glycosides, flavonoid glycosides, chalcones or chalcone glycosides, hydrolysable tannins, non-hydrolysable tannins, flavones, other polyphenols, terpenoid bitter substances, absinthin from wormwood, amarogentin from gentian, metal salts, pharmaceutically active ingredients: fluoroquinolone antibiotics, beta-lactam antibiotics, ambroxol, propylthiouracil [PROP], aspirin (acetyl salicylic acid), salicin, paracetamol (acetaminophene), ibuprofen, naproxen, ambroxol, guafenesin, omeprazole, pantoprazole, dextromorphane, or quinine, vitamins, denatonium benzoate or other denatonium salts, sucralose octaacetate, urea, unsaturated fatty acids, and amino acids, and/or the both sweet- and unpleasant-tasting substance is selected from the group consisting of steviolglycosides, rubusoside, dulcoside, mogroside, phyllodulcin, glycyrrhetin acid or extracts of *Stevia* ssp., Luo Han Guo, *Rubus* suavissimus, *Hydrangea dulcis, Mycetia balansae, Glycyrrhyza glabra*, magap, sodium cyclamate, acesulfame K, neohesperidine dihydrochalcone, naringin hydrochalcone, saccharin, saccharin sodium salt, aspartame, superaspartame, neotame, alitame, sucralose, lugduname, carrelame, sucrononate, and sucrooctate.

2. The method of claim 1, wherein the method masks, reduces, and/or suppresses an unpleasant taste impression and/or modulates a cooling, an umami, a fruity, and/or a spicy taste impression of
(1) preparations serving for nourishment, food supplements, oral care or pleasure,
(2) cosmetic preparations,
(3) pharmaceutical preparations intended for oral administration,
(4) flavouring mixtures for use in one of the preparations mentioned in (1) to (3), or
(5) semi-finished products for manufacturing one of the preparations mentioned in (1)-(3).

3. A method for masking, reducing, and/or suppressing an unpleasant taste impression of an unpleasant tasting substance, the method comprising mixing:
(i) hesperetin dihydrochalcone (I) (3-(3-Hydroxy-4-methoxy-phenyl)-1-(2,4,6-trihydroxyphenyl)propan-1-one),

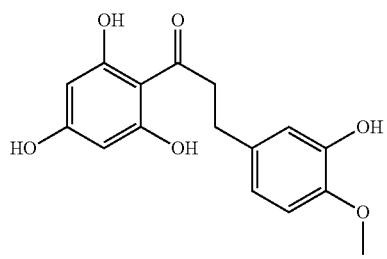

(I)

a salt of the hesperetin dihydrochalcone (I), a mixture of a plurality of salts of the hesperetin dihydrochalcone (I), or a mixture of the hesperetin dihydrochalcone (I) and a salt or a plurality of salts of the hesperetin dihydrochalcone (I), and
(ii) an unpleasant tasting substance selected from the group consisting of xanthine alkaloids, xanthines, alkaloids, phenolic glycosides, flavonoid glycosides, chalcones or chalcone glycosides, hydrolysable tannins, non-hydrolysable tannins, flavones, other polyphenols, terpenoid bitter substances, absinthin from wormwood, amarogentin from gentian, metal salts, pharmaceutically active ingredients: fluoroquinolone antibiotics, beta-lactam antibiotics, ambroxol, propylthiouracil [PROP], aspirin (acetyl salicylic acid), salicin, paracetamol (acetaminophene), ibuprofen, naproxen, ambroxol, guafenesin, omeprazole, pantoprazole, dextromorphane, or quinine, vitamins, denatonium benzoate or other denatonium salts, sucralose octaacetate, urea, unsaturated fatty acids, and amino acids.

4. The method of claim 3, wherein the unpleasant taste impression is a bitter, sour, and/or astringent taste impression and the unpleasant tasting substance is a bitter, sour, and/or astringent tasting substance.

5. The method of claim 3, wherein the unpleasant taste impression is a bitter taste impression and the unpleasant tasting substance is a bitter tasting substance.

6. The method of claim 5, wherein the method also synergistically intensifies a sweet-taste impression of a sweet-tasting substance.

7. The method of claim 3, wherein the unpleasant tasting substance is an alkaloid.

8. The method of claim 7, wherein the alkaloid is quinine hydrochloride.

9. The method of claim 7, wherein the method also synergistically intensifies a sweet-taste impression of a sweet-tasting substance.

10. The method of claim 9, wherein the sweet tasting substance is sucrose.

11. A method for modulating a cooling, an umami, a fruity, and/or a spicy taste impression of a cooling, an umami, a fruity, and/or a spicy tasting substance, the method comprising mixing:
(i) hesperetin dihydrochalcone (I) (3-(3-Hydroxy-4-methoxy-phenyl)-1-(2,4,6-trihydroxyphenyl)propan-1-one),

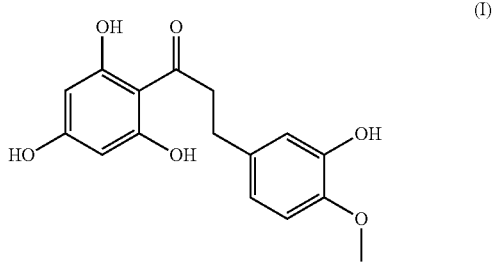 [SMILES: COc1ccc(CCC(=O)c2c(O)cc(O)cc2O)cc1O]

(I)

a salt of the hesperetin dihydrochalcone (I), a mixture of a plurality of salts of the hesperetin dihydrochalcone (I), or a mixture of the hesperetin dihydrochalcone (I) and a salt or a plurality of salts of the hesperetin dihydrochalcone (I), and
(ii) a cooling, an umami, a fruity and/or a spicy tasting substance.

12. The method of claim 11, wherein the method also synergistically intensifies the sweet-taste impression of a sweet-tasting substance.

* * * * *